(12) United States Patent
Kobayashi

(10) Patent No.: US 11,562,511 B2
(45) Date of Patent: Jan. 24, 2023

(54) MEDICAL IMAGE PROCESSING APPARATUS, X-RAY DIAGNOSTIC APPARATUS, AND STORAGE MEDIUM

(71) Applicant: Canon Medical Systems Corporation, Otawara (JP)

(72) Inventor: Yoshimasa Kobayashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 92 days.

(21) Appl. No.: 16/874,728

(22) Filed: May 15, 2020

(65) Prior Publication Data

US 2020/0372693 A1    Nov. 26, 2020

(30) Foreign Application Priority Data

May 20, 2019  (JP) .............................. JP2019-094504

(51) Int. Cl.
*G06T 11/00* (2006.01)
*G06T 7/11* (2017.01)
(Continued)

(52) U.S. Cl.
CPC ............ *G06T 11/008* (2013.01); *A61B 6/025* (2013.01); *A61B 6/469* (2013.01); *G06T 7/11* (2017.01);
(Continued)

(58) Field of Classification Search
CPC ........... A61B 6/025; A61B 6/032; A61B 6/08; A61B 6/4035; A61B 6/463; A61B 6/465; A61B 6/466; A61B 6/469; A61B 6/486; A61B 6/502; A61B 6/5223; A61B 6/545; G06T 7/0012; G06T 7/11; G06T 11/008; G06T 2207/10112; G06T 2207/10116; G06T 2207/30068; G06T 2211/436
See application file for complete search history.

(56) References Cited

U.S. PATENT DOCUMENTS 8,184,890 B2 * 5/2012 Zhang ................. A61B 6/5235
                                                        382/128
10,893,844 B1 * 1/2021 Douglas ................ A61B 90/39
(Continued)

FOREIGN PATENT DOCUMENTS

JP        2017-047079 A      3/2017

OTHER PUBLICATIONS

Duan et al. "Matching corresponding regions of interest on craniocaudal and medio-lateral oblique view mammograms." IEEE Access 7 (Mar. 2019): 31586-31597. (Year: 2019).*

*Primary Examiner* — Katrina R Fujita
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry designates a region of interest in a first tomogram among multiple tomograms which are based on tomosynthesis imaging performed with a subject compressed in a first direction. The processing circuitry specifies a second tomogram corresponding to the region of interest from among multiple tomograms which are based on tomosynthesis imaging performed with the subject compressed in a second direction different from the first direction.

11 Claims, 22 Drawing Sheets

(51) Int. Cl.
*A61B 6/02* (2006.01)
*A61B 6/00* (2006.01)

(52) U.S. Cl.
CPC ..... *A61B 6/502* (2013.01); *G06T 2207/10112* (2013.01); *G06T 2207/10116* (2013.01); *G06T 2207/30068* (2013.01)

(56) References Cited

U.S. PATENT DOCUMENTS

| | | | | |
|---|---|---|---|---|
| 2008/0152086 | A1* | 6/2008 | Hall | A61B 6/5235 378/98.2 |
| 2012/0014578 | A1* | 1/2012 | Karssemeijer | G06T 7/0012 382/131 |
| 2014/0082542 | A1* | 3/2014 | Zhang | G16H 30/40 715/771 |
| 2014/0343420 | A1* | 11/2014 | Zhang | A61B 8/469 600/437 |
| 2015/0077430 | A1* | 3/2015 | Conroy | G06T 11/60 345/589 |
| 2015/0139518 | A1* | 5/2015 | Oohashi | G06T 7/0016 382/131 |
| 2015/0356245 | A1* | 12/2015 | Kozu | G16H 50/70 705/2 |
| 2016/0110875 | A1* | 4/2016 | Sugiyama | G06T 7/0012 382/131 |
| 2018/0033143 | A1* | 2/2018 | Buelow | A61B 6/5217 |
| 2018/0070892 | A1* | 3/2018 | Sugiyama | A61B 6/502 |

* cited by examiner

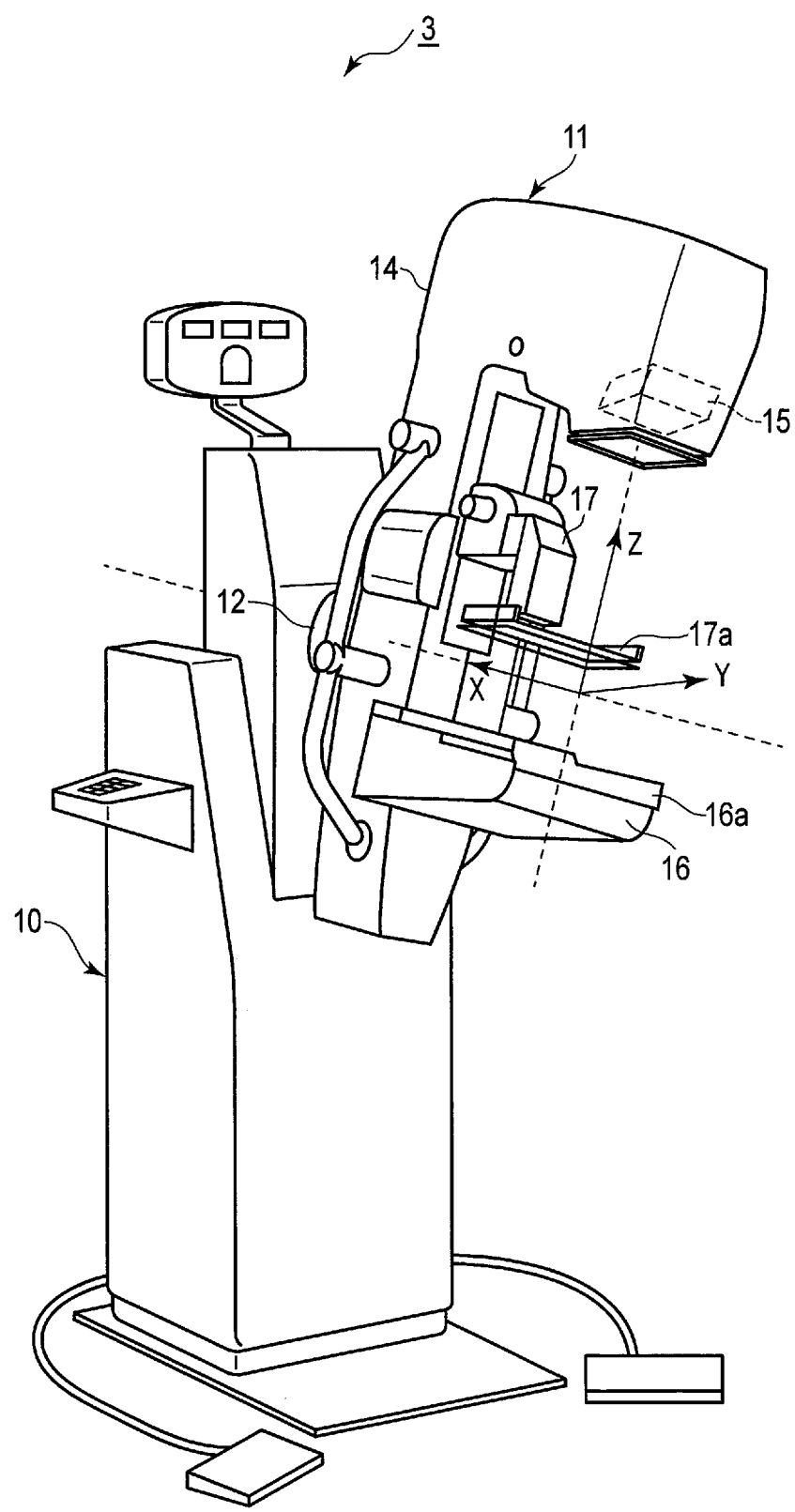
F I G. 3

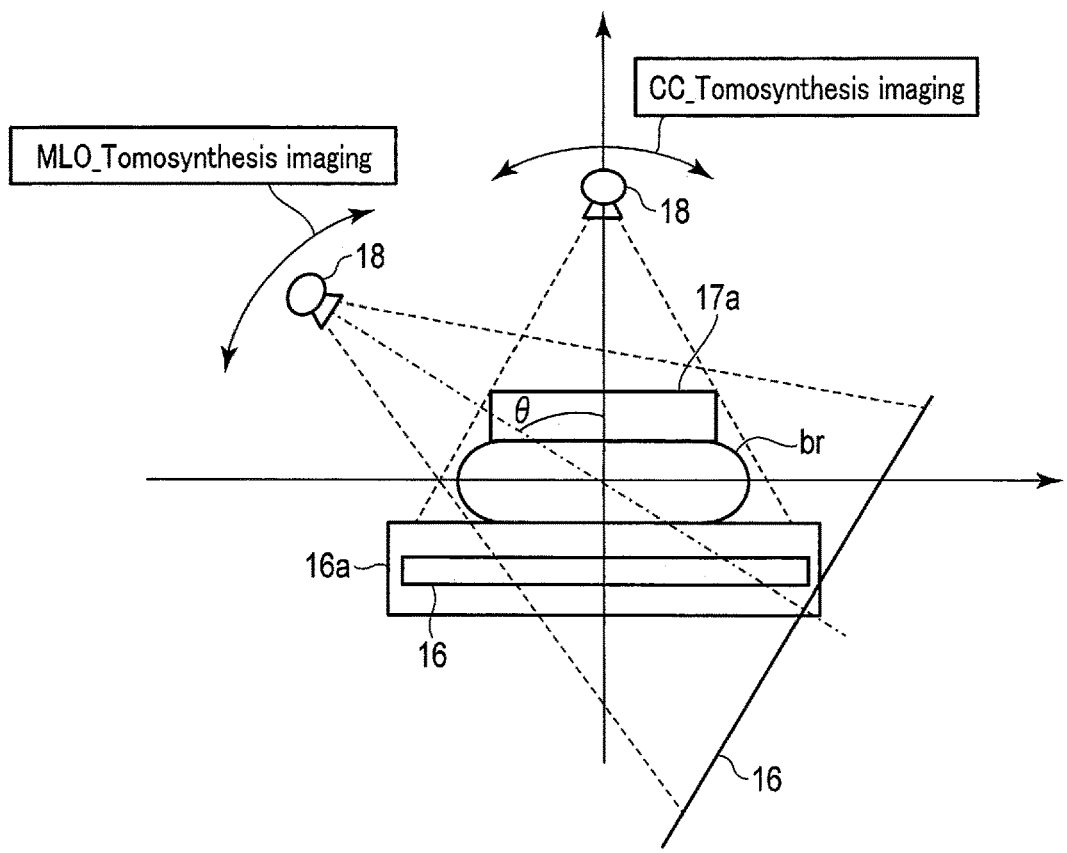
F I G. 4
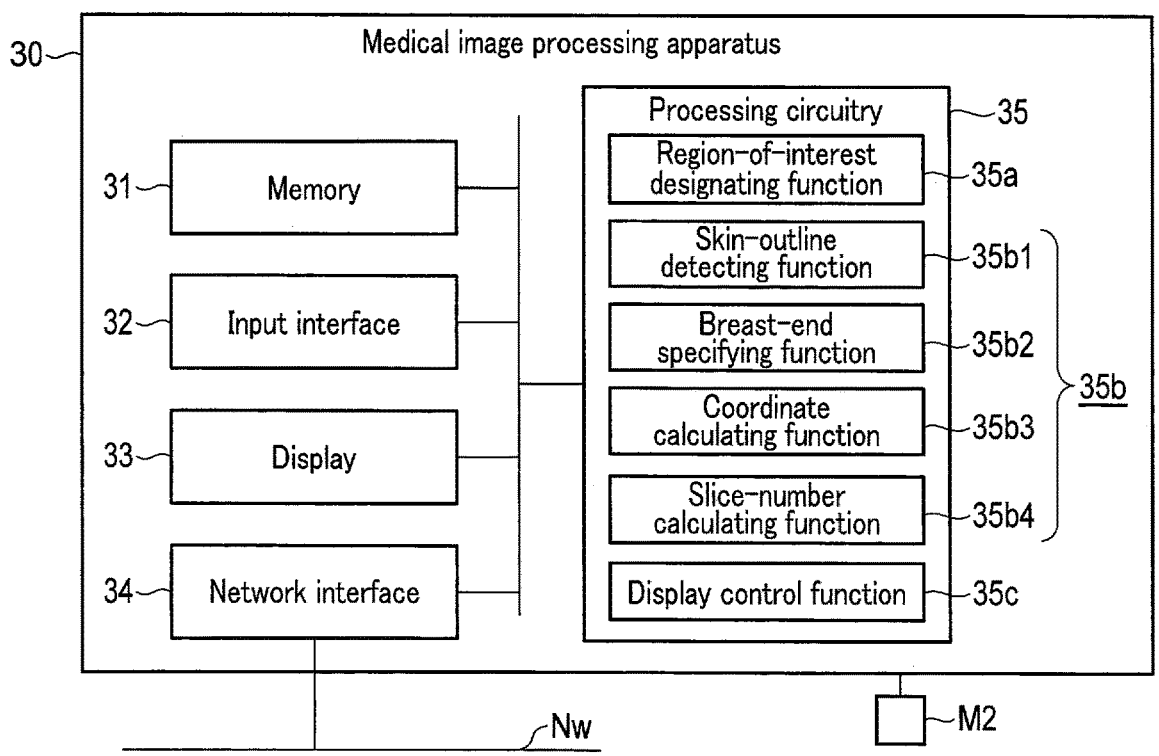
F I G. 5

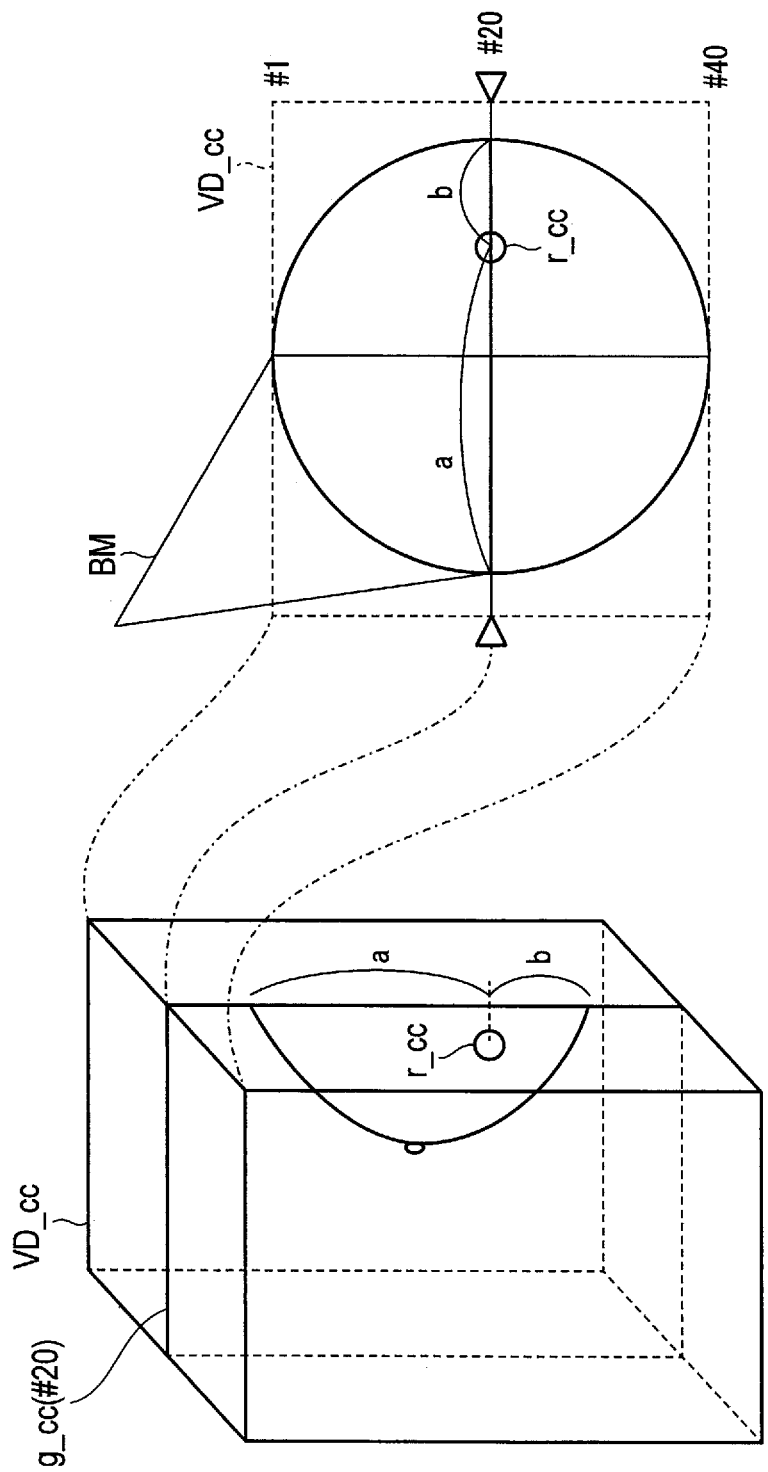
F I G. 7

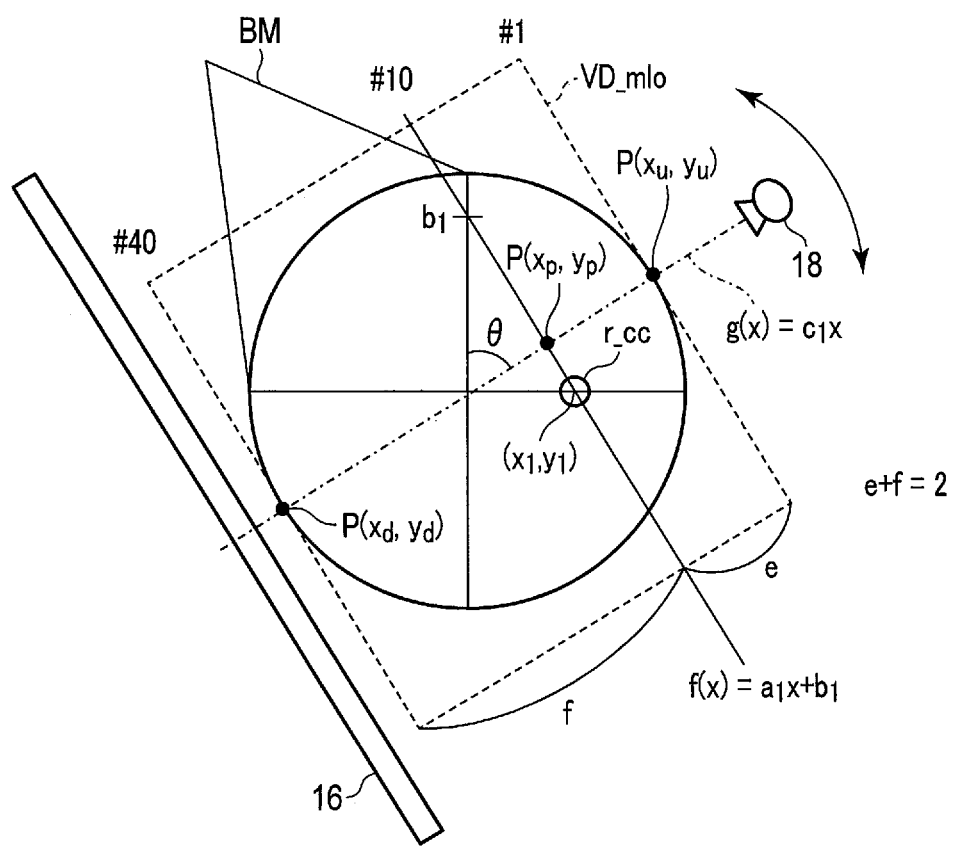
F I G. 11

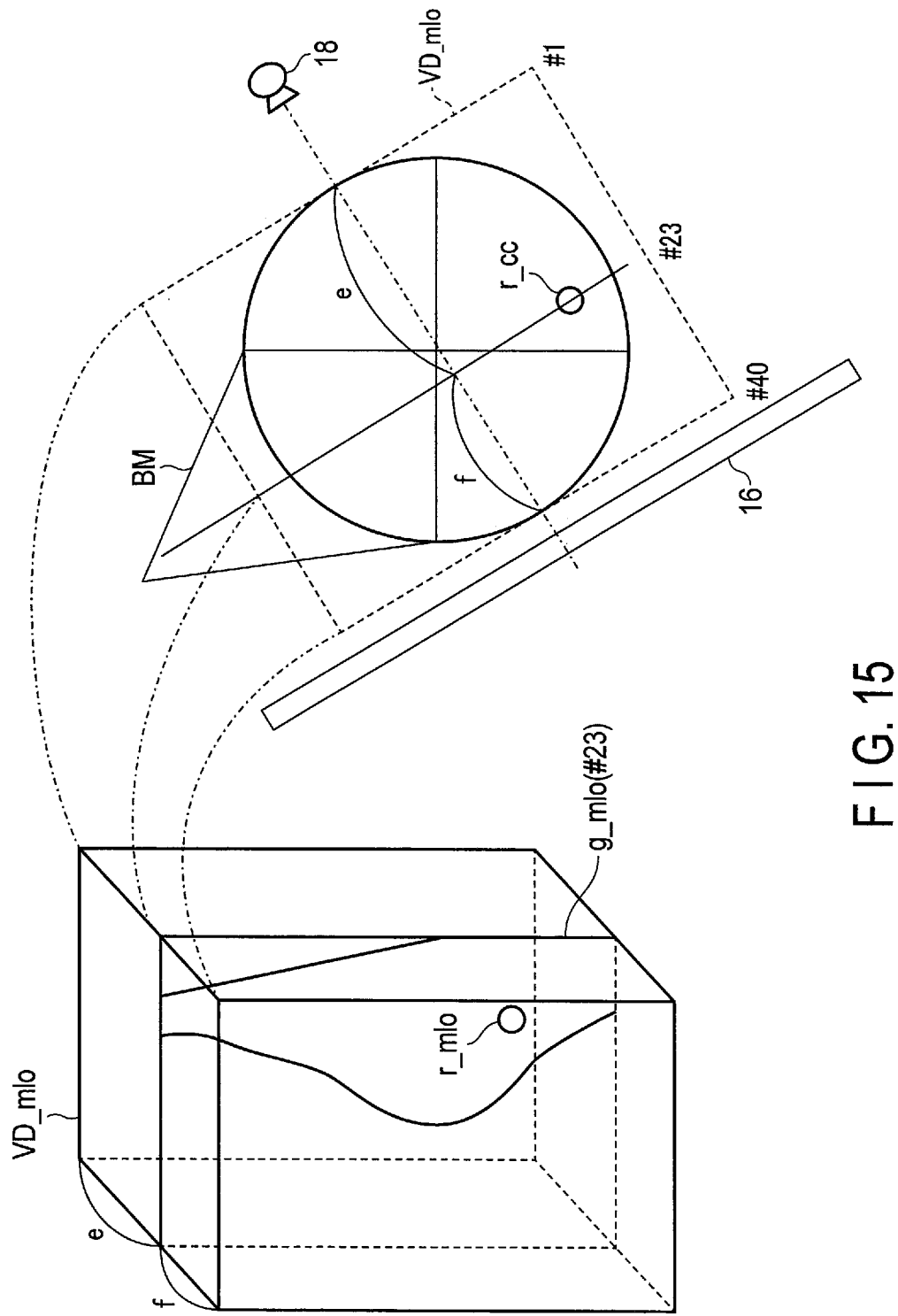
F I G. 15

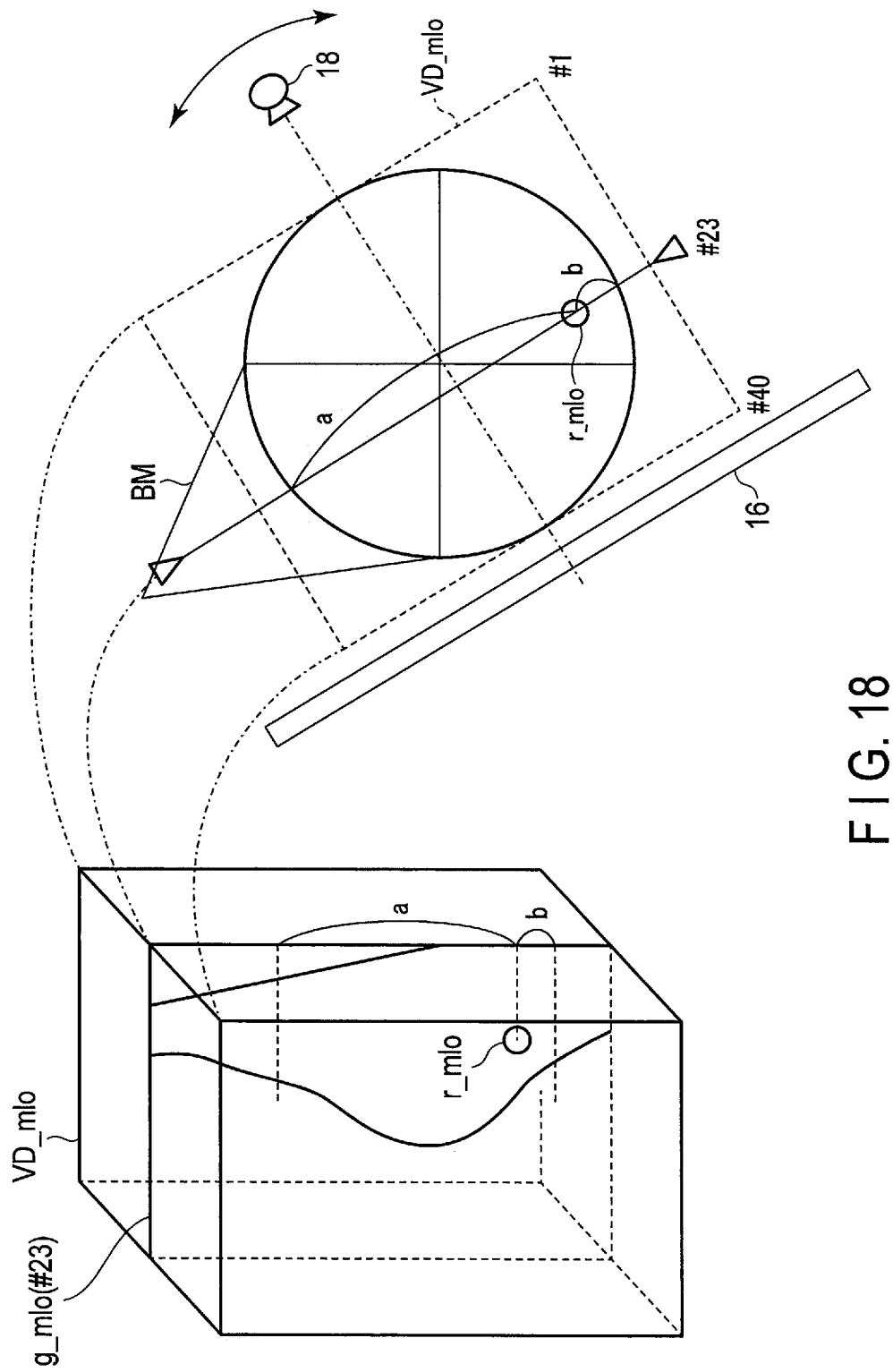
F I G. 18

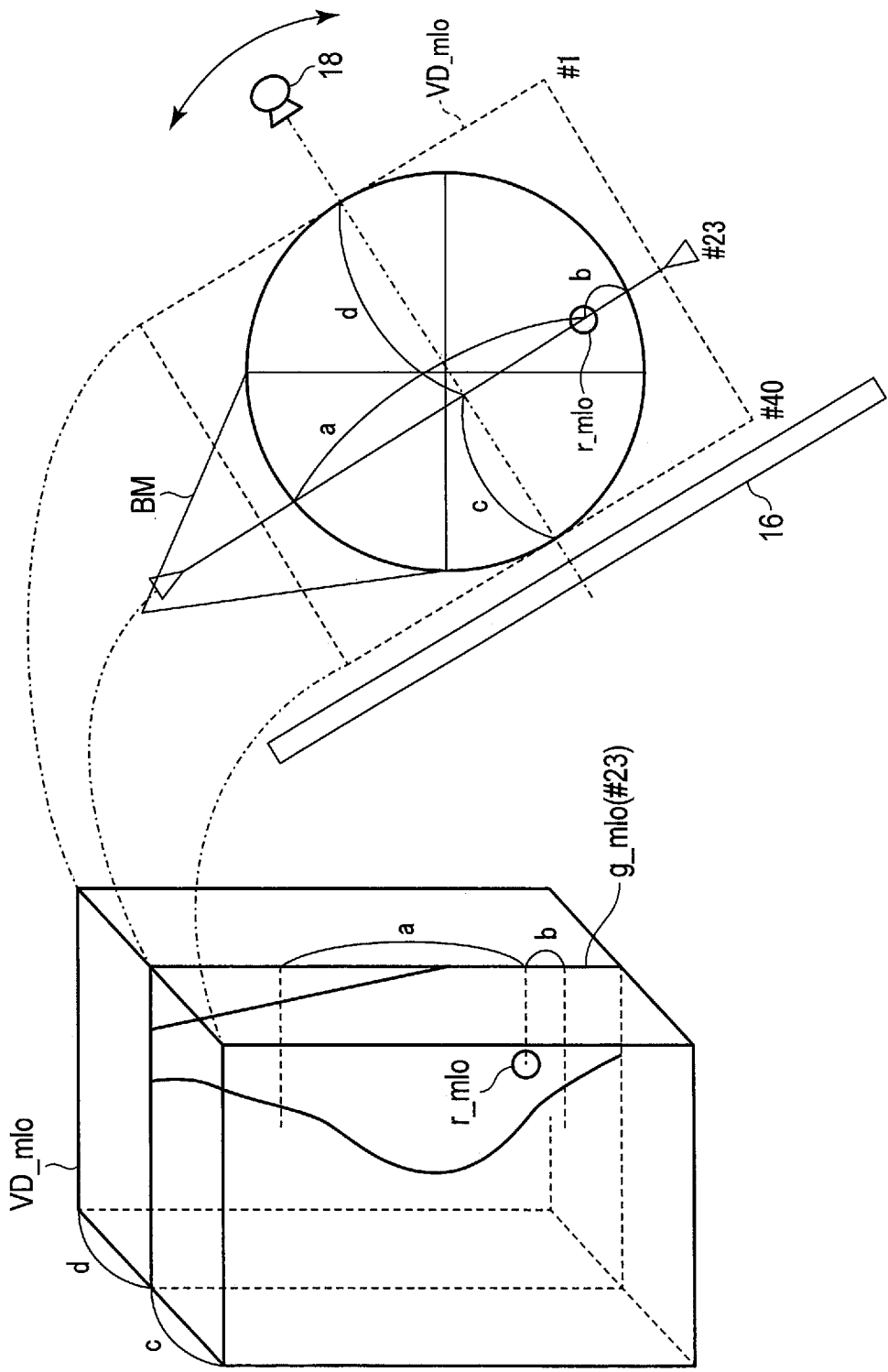
F I G. 19

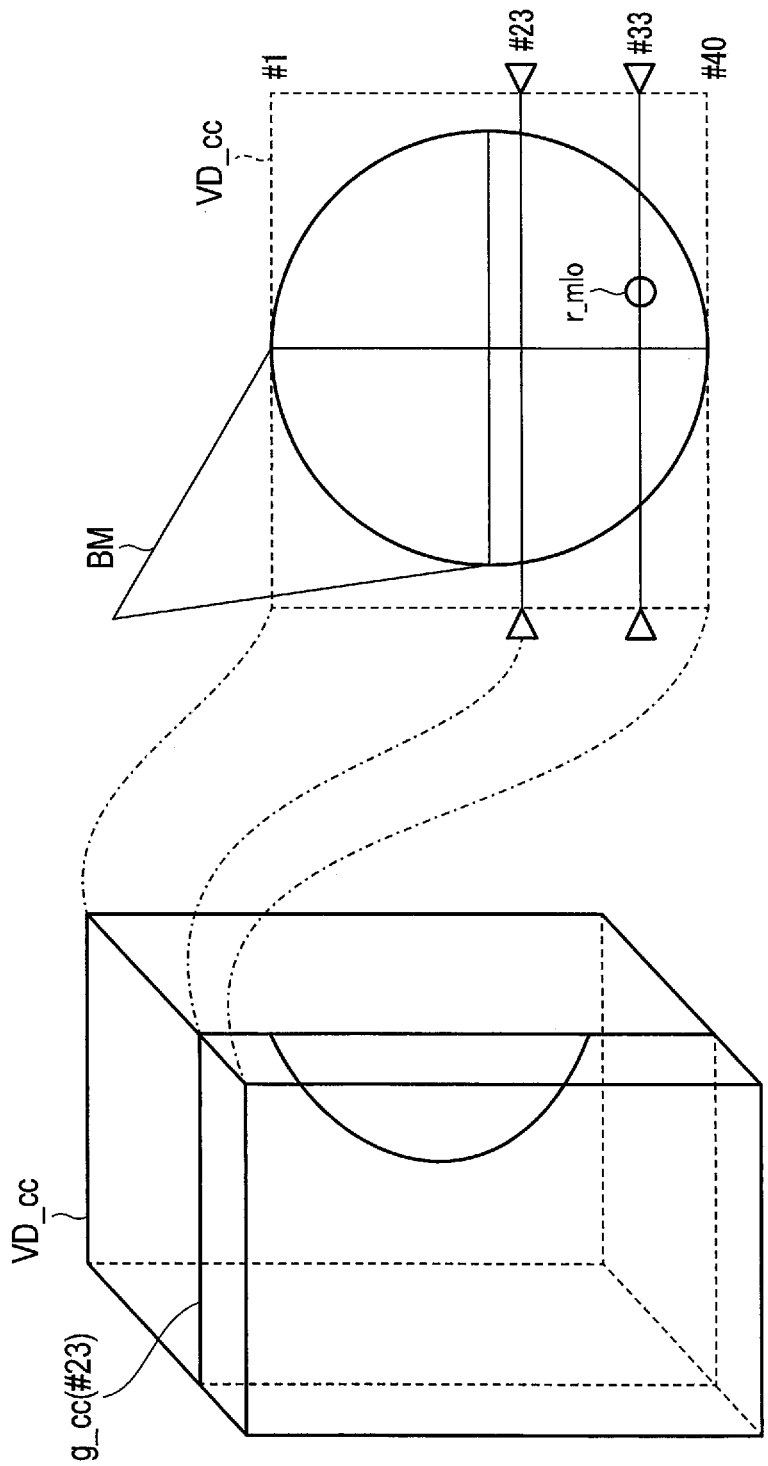
F I G. 20

MEDICAL IMAGE PROCESSING APPARATUS, X-RAY DIAGNOSTIC APPARATUS, AND STORAGE MEDIUM

CROSS-REFERENCE TO RELATED APPLICATIONS

This application is based upon and claims the benefit of priority from prior Japanese Patent Application No. 2019-94504, filed May 20, 2019, the entire contents of which are incorporated herein by reference.

FIELD

Embodiments described herein relate generally to a medical image processing apparatus, an X-ray diagnosis apparatus, and a storage medium.

BACKGROUND

Diagnosis with mammary gland images, adopted for breast cancer screening, etc. in these years, includes diagnostic reading or interpretation of mammograms taken from two different imaging directions by an X-ray diagnostic apparatus. The two imaging directions may be selected as appropriate from the directions including, for example, a craniocaudal (CC) projection direction and a mediolateral oblique (MLO) projection direction. For use in such mammary gland image diagnosis, a three-dimensional imaging technique called tomosynthesis is growing popular now, besides the conventionally-adopted two-dimensional imaging technique.

Tomosynthesis is an imaging technique for generating multiple tomograms by three-dimensionally reconstructing medical images which have been acquired at multiple angles along with the movement of an X-ray source. Tomosynthesis imaging of a breast can create tomograms involving reduced overlap of mammary glands.

While guidelines or the like for how to interpret tomograms are not available, there are, according to the research by the present inventor, instances where the interpretation is performed with reference to the comparison made between each of multiple first tomograms acquired in one imaging direction and each of multiple second tomograms acquired in another imaging direction. The imaging directions here each embrace multiple angles at which the X-ray source is positioned during the tomosynthesis imaging (which are, strictly speaking, multiple directions for three-dimensional shooting actions), but for the sake of description, the imaging directions are each assumed to be represented by the middle angle among such multiple angles (middle shooting direction which may be the CC direction, the MLO direction, or other direction).

In said instances, specifying a second tomogram that corresponds to a given region of interest in the first tomograms is a burden on operators. In order to mitigate it, a technique has been developed by which a region of interest designated in the first tomograms is associated with the second tomograms through a schema. For this technique, view-section correspondence information associating a position of a view section with a location in a schema is generated for each of the first tomograms and the second tomograms, and based on the view-section correspondence information for one imaging direction, region-of-interest correspondence information associating a region of interest with a set of tomograms for the other imaging direction is generated. These view-section correspondence information and region-of-interest correspondence information enable the burden-mitigating technique to be implemented based on the view-section correspondence information for a set of tomograms in which a region of interest has been designated. With this technique, operators who are referring to the second tomograms can visually recognize the location of the applicable area that corresponds to the region of interest designated in the first tomograms.

Such a burden-mitigating technique normally serves well, but the present inventor sees room for alternatives as the technique must rely on use of the view-section correspondence information and the region-of-interest correspondence information. It is expected that realizing the alternative will give birth to an advantageous configuration where only designating a region of interest in the first tomograms acquired in one imaging direction allows for specifying the corresponding second tomogram acquired in another imaging direction.

BRIEF DESCRIPTION OF THE DRAWINGS

FIG. 3 is a perspective view showing, as one example, appearance of an X-ray imaging stand according to the embodiment.

FIG. 4 is a front view of a part of the X-ray diagnostic apparatus according to the embodiment, seen from the side of a subject, and depicts an instance where the subject's right breast is undergoing tomosynthesis imaging.

FIG. 5 is a block diagram showing an exemplary configuration of a medical image processing apparatus according to the embodiment.

FIG. 7 is a diagram showing one example of a tomogram and a body mark upon performing tomosynthesis imaging for the subject's right breast in the CC direction in the context of the embodiment.

FIG. 11 is a diagram for explaining an exemplary operation according to the embodiment.

FIG. 15 is a diagram for explaining another exemplary operation according to the embodiment.

FIG. 18 is a diagram showing one example of a tomogram and a body mark upon performing tomosynthesis imaging for the subject's right breast in the MLO direction in the context of a first modification of the embodiment.

FIG. 19 is a diagram for explaining an exemplary operation according to the first modification of the embodiment.

FIG. 20 is a diagram showing one example of a tomogram and a body mark upon performing tomosynthesis imaging for the subject's right breast in the CC direction in the context of the first modification of the embodiment.

DETAILED DESCRIPTION

According to one embodiment, a medical image processing apparatus includes processing circuitry. The processing circuitry designates a region of interest in a first tomogram among multiple tomograms which are based on tomosynthesis imaging performed with a subject compressed in a first direction. The processing circuitry specifies a second tomogram corresponding to the region of interest from among multiple tomograms which are based on tomosynthesis imaging performed with the subject compressed in a second direction different from the first direction.

This achieves the configuration where only designating a region of interest in the first tomograms acquired in one imaging direction allows for specifying which of the second tomograms acquired in another imaging direction corresponds to the region of interest.

Now, a certain embodiment will be described with reference to the drawings. For the embodiment, the description will assume an exemplary case where the processing circuitry as mentioned above designates a region of interest in one of multiple first tomograms acquired by imaging the right breast of a subject in a first imaging direction, and specifies a second tomogram that includes an area corresponding to this region of interest from among multiple second tomograms acquired by imaging the breast in a second imaging direction different from the first imaging direction.

Figure 1:
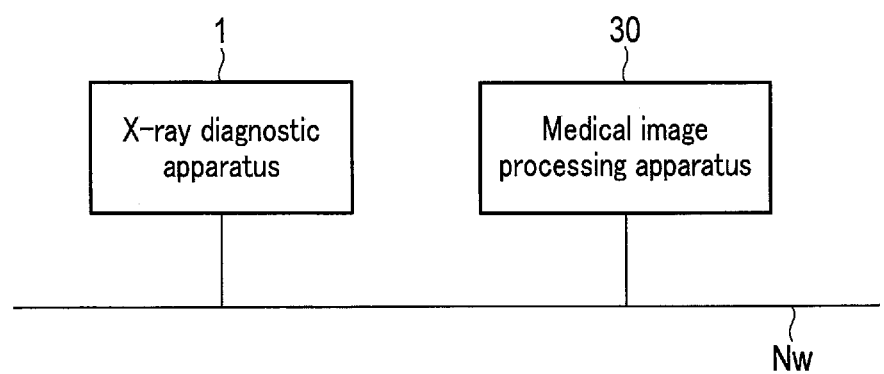
FIG. 1 is a block diagram showing an exemplary configuration of a medical image processing system according to an embodiment.

FIG. 1 is a block diagram showing a configuration of a medical image processing system according to this embodiment. The medical image processing system includes an X-ray diagnostic apparatus 1 and a medical image processing apparatus 30 which are adapted to communicate with each other via a network Nw. Note that the medical image processing system may further include an ultrasound diagnostic apparatus connected via the network Nw.

Figure 2:
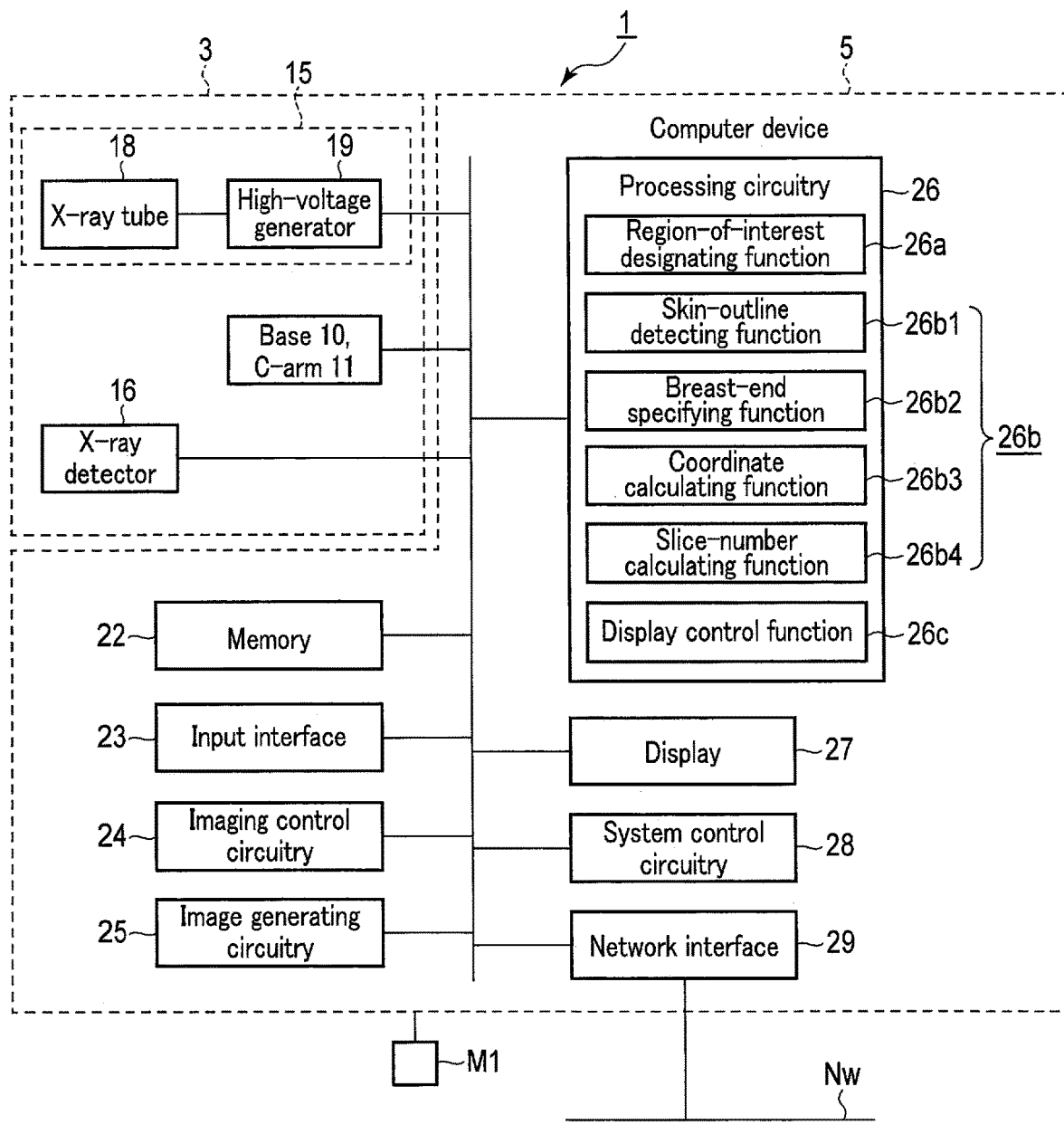
FIG. 2 is a block diagram showing an exemplary configuration of an X-ray diagnostic apparatus according to the embodiment.
Figure 6:
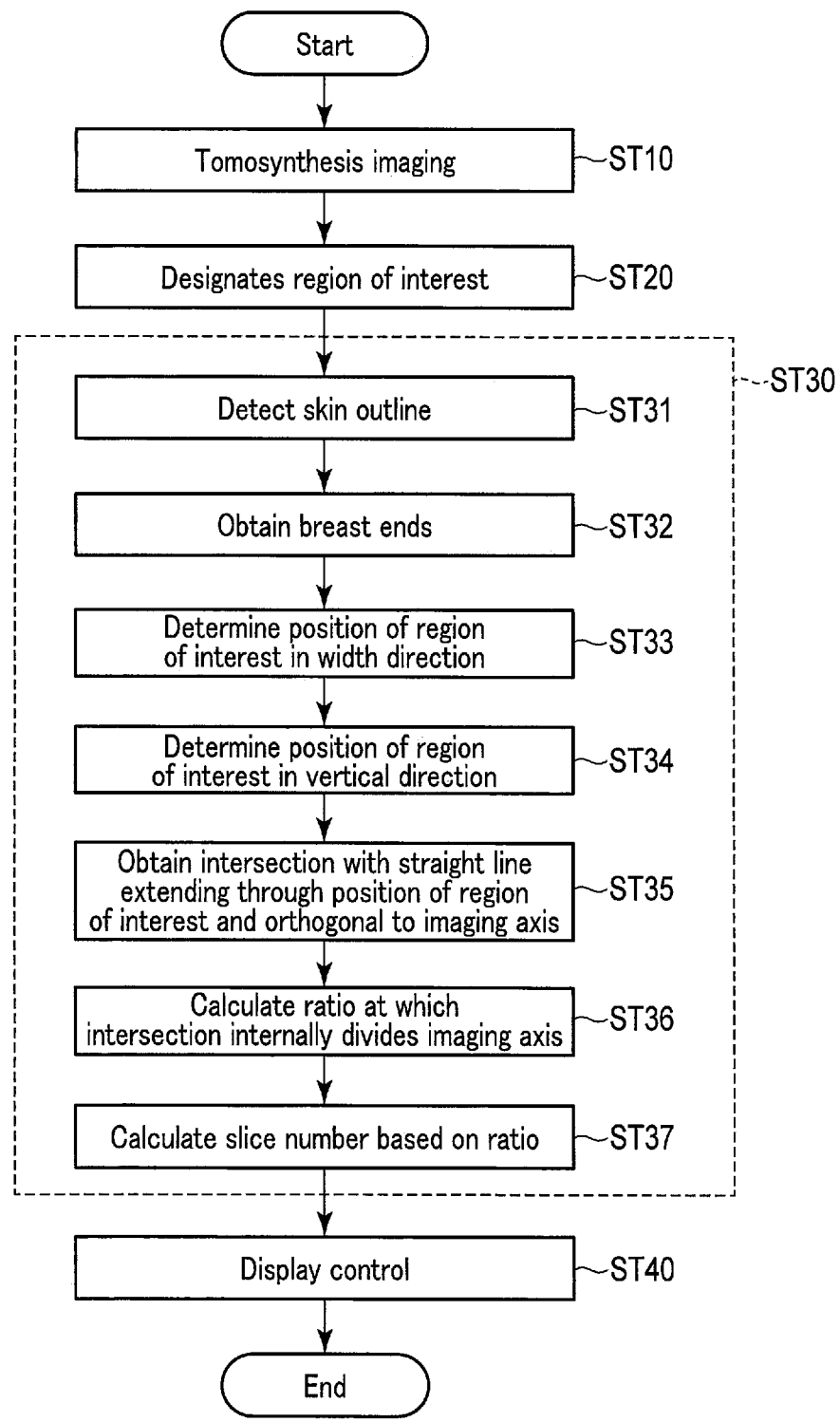
FIG. 6 is a flowchart for explaining an exemplary operation according to the embodiment.

The X-ray diagnostic apparatus 1 includes an X-ray imaging stand 3 and a computer device 5 as shown in FIGS. 2 to 4.

The X-ray imaging stand 3 includes a base 10 and a C-arm 11. The C-arm 11 is attached to a shaft 12 projecting from the base 10. The C-arm 11 is thus supported by the base 10 so that it can rotate about the center of the shaft 12, i.e., a central axis X for rotation. Rotation of the C-arm 11 enables operations for normal imaging and tomosynthesis imaging based on various projection directions including a craniocaudal (CC) direction, a mediolateral (ML) direction, and a mediolateral oblique (MLO) direction. Note that the tomosynthesis imaging generally adopts the CC direction and the MLO direction as its two imaging directions, from among the CC direction, the ML direction, and the MLO direction, and so on.

The C-arm 11 is constituted by an arm body 14 furnished with an X-ray generator 15, an X-ray detector 16, and a compression unit 17. The X-ray generator 15 and the X-ray detector 16 are arranged at the respective ends of the arm body 14. The compression unit 17 is arranged midway between the X-ray generator 15 and the X-ray detector 16.

The X-ray generator 15 includes an X-ray tube 18 and a high-voltage generator 19. The X-ray tube 18 is adapted to receive a tube voltage application and a filament current supply from the high-voltage generator 19 to output X-rays toward the compression unit 17 for a predetermined X-ray continuation period. The tube voltage for application and the X-ray continuation period are adjusted into values that are suitable for imaging operations, based on control signals received from later-described imaging control circuitry 24.

The X-ray tube 18 includes a cathode filament and an anode. The anode may include an Mo anode formed of molybdenum (Mo), an Rh anode formed of rhodium (Rh), an Mo—Rh anode formed of a mixture of Mo and Rh, and so on. These anodes may be provided so that they can discretionarily be switched according to the control signals from the imaging control circuitry 24.

With the filament current supply, the cathode filament is heated and generates thermal electrons. With the tube voltage application between the cathode filament and the anode, the generated thermal electrons are caused to collide with the anode. The thermal electrons colliding with the anode in this way generate X-rays. As the thermal electrons fly and collide with the anode, a tube current flows. The tube current is adjusted by the filament current. The tube current is adjusted by the filament current. The X-ray dose during an imaging operation is controlled by adjusting a tube current time product, which is a product of the tube current multiplied by the X-ray continuation period (time), according to the control signals from the imaging control circuitry 24.

The X-ray tube 18 is provided with a radiation quality filter for altering the radiation quality of the X-rays generated. The radiation quality filter may include an Mo filter formed of Mo, an Rh filter formed of Rh, an Al filter formed of aluminum (Al), a filter formed of a mixture of such materials, and so on. These filters may be provided so that they can discretionarily be switched according to the control signals from the imaging control circuitry 24.

The compression unit 17 includes a compression plate 17a which is supported by the C-arm 11 in such a manner as to be capable of making approaching and distancing movement with respect to a detection plane 16a of the X-ray detector 16. The compression unit 17 moves the compression plate 17a according to the control signals from the imaging control circuitry 24 so that the subject's breast is pressed against the detection plane 16a and set to a predetermined thickness state. For example, as shown in FIG. 4, when the subject's right breast Br is subjected to tomosynthesis imaging, the thickness of this right breast Br is brought into a predetermined state.

The X-ray detector 16 is supported by the C-arm 11 in such a manner as to be capable of approaching and moving away from the X-ray tube 18 along an imaging axis connecting the plane center of the detection plane 16a and the focal point of the X-ray tube 18. The X-ray detector 16 is a digital detector which may be a flat panel detector or other detector, adapted to detect X-rays transmitted through the breast. Such a digital detector includes multiple direct-conversion type semiconductor detecting elements for converting incident X-rays directly into electrical signals, or multiple indirect-conversion type semiconductor detecting elements for converting incident X-rays into light by fluorescent components and then convert the light into electrical signals. These semiconductor detecting elements are arrayed in a two-dimensional grid. The digital detector may additionally include an amplifier circuit and an A/D converter circuit for the semiconductor detecting elements, e.g., photodiodes. Thus, signal charges occurring at the multiple semiconductor detecting elements upon X-ray incident are relayed through the amplifier circuit and the A/D converter circuit, and output as digital signals to the computer device 5.

The computer device 5, for common use with the X-ray imaging stand 3, includes a memory 22, an input interface 23, the aforementioned imaging control circuitry 24, image generating circuitry 25, processing circuitry 26, a display 27, a system control circuitry 28, and a network interface 29. Among these components of the computer device 5, the memory 22, the input interface 23, the processing circuitry 26, the display 27, and the network interface 29 have the functions similar to those of the later-described components of the medical image processing apparatus 30. That is, part of the computer device 5 may be realized by incorporation of the medical image processing apparatus 30.

The memory 22 is constituted by a memory main part for storing electric information, such as a read only memory (ROM), a random access memory (RAM), a hardware disk drive (HDD), an image memory, etc. The memory 22 is also constituted by peripheral circuitry pertaining to the memory pain part, such as a memory controller, a memory interface, etc. The memory 22 is adapted to store one or more medical images and programs. Examples of the medical images include mammograms acquired under normal imaging, and tomograms acquired under tomosynthesis imaging. For example, the memory 22 stores, in conjunction with tomosynthesis imaging, multiple first tomograms acquired by imaging the subject's breast in a first imaging direction, and multiple second tomograms acquired by imaging the breast in a second imaging direction different from the first imaging direction. In the context of the embodiment, the first imaging direction and the second imaging direction are assumed to be the CC direction and the MLO direction, respectively. The multiple tomograms are each assigned a slice number, and can accordingly be specified or identified by the assigned slice number. For example, when the compressed breast as shown in FIG. 4 has a thickness of 40 mm, and the total number of slices is 40, the tomograms may be assigned the respective slice numbers "#1", "#2", . . . , and "#40" sequentially from the top. Further, the first tomograms and the second tomograms may each include, for example, accessory information (not illustrated) containing corresponding imaging conditions, code indicative of the imaging direction (imaging angle) used at the imaging, a code indicative of whether the imaged subject is the right breast or the left breast, and so on. The program stored in the memory 22 may cause a computer to implement, for example, a designating function and a specifying function. This designating function corresponds to a region-of-interest designating function 26a, which will be described later. The specifying function corresponds to a specifying function 26b, described later. The program may further cause the computer to implement a display control function. This display control function corresponds to a display control function 26c, also described later. Additionally, such a program may be, for example, installed in the computer from the network or a non-transitory computer-readable storage medium M1 in advance, so that the program will cause the processor of the computer to perform the designating function and the specifying function. The program includes, for example, instructions for the processor to perform each function.

The input interface 23 is realized by components for an operator to input various instructions, commands, information, selections, settings, etc. to the computer device 5, and such components include a trackball, switch buttons, a mouse, a keyboard, a touch pad which allows an input operation through contacting the operation screen, and a touch panel display which integrates a display screen and a touch pad. The input interface 23 is connected to the imaging control circuitry 24, the processing circuitry 26, etc., and adapted to convert input operations received from the operator into electric signals and to output the electric signals to the imaging control circuitry 24, the processing circuitry 26, etc. Note that, when the following explanation of the computer device 5 mentions "operator's operation", it may be taken as "operation on the input interface 23 by the operator". Also, in the disclosure herein, the input interface 23 is not limited to physical operating components such as a mouse and a keyboard. That is, the examples of the input interface 23 also include processing circuitry for electrical signals that is adapted to receive an electrical signal corresponding to an input operation from an external input device separate from the apparatus, and to output this electrical signal to the imaging control circuitry 24, the processing circuitry 26, etc.

The input interface 23 serves as an operation panel for setting imaging conditions (tube voltage, tube current time product, anode material, radiation quality filter material, breast thickness, distance between the X-ray focal point and the X-ray detector, magnification rate, etc.) to the imaging control circuitry 24. Using the input interface 23, a code indicative of whether the imaging is performed on the right breast or the left breast is also set to the imaging control circuitry 24. The input interface 23 also serves as an interface for manipulating the C-arm 11, and operating the input interface 23 can thus rotate the C-arm 11 about a Z-axis and set it in a desired position. The imaging direction is determined according to the set position of the C-arm 11.

The imaging control circuitry 24 includes a processor and a memory (not illustrated) to control each component of the X-ray imaging stand 3 based on the imaging conditions (tube voltage, tube current time product, anode material, radiation quality filter material, breast thickness, distance between the X-ray focal point and the X-ray detector, magnification rate, etc.) set via the input interface 23, so that the X-ray imaging stand 3 performs the X-ray imaging according to the setting.

The image generating circuitry 25 generates mammogram data, etc. based on the output of the X-ray detector 16. Normally, an area representing a living object in the images acquired by mammography imaging covers not only a breast region but also a region other than the breast region, such as a greater pectorals muscle region.

The processing circuitry 26 reads the tomograms with accessory information and also the program from the memory 22 according to an instruction input by the operator through the input interface 23, and controls the computer device 5 based on these. For example, the processing circuitry 26 is a processor to realize, in addition to existing functions, various functions for assisting the interpretation of medical images according to the program read from the memory 22. Such various functions include, for example, the aforementioned region-of-interest designating function 26a, specifying function 26b, and display control function 26c. The specifying function 26b may include, for example, a skin-outline detecting function 26b1, a breast-end determining function 26b2, a coordinate calculating function 26b3, and a slice-number calculating function 26b4, as appropriate. The display control function 26c may be performed by other computer (not illustrated), instead of the processing circuitry 26. In such instances, for example, an internal component functioning as a medical image processing apparatus in the computer device 5 may operate as a server device, and said other computer may accordingly operate as a client device that displays the second tomogram specified by the server device.

The region-of-interest designating function 26a designates a region of interest in a first tomogram among multiple tomograms which are based on tomosynthesis imaging performed in the state where the subject is compressed in a first direction. For example, the region-of-interest designating function 26a designates a region of interest in one of multiple first tomograms acquired by imaging the subject's breast in a first imaging direction. In this example, the first direction is the first imaging direction, and the first imaging direction is the CC direction. Also in this example, the "subject" as an imaging target is the "subject's breast" or a "breast". When the term "breast" appears without "subject's", it may be taken as "subject". Designating the region of interest may be performed according to an operation on the input interface 23 by the operator, or according to a result of detecting a pathological region through mammography computer-aided diagnosis (CAD). The region-of-interest designating function 26a is one example of a designator.

The specifying function 26b specifies a second tomogram corresponding to the region of interest from among multiple tomograms which are based on tomosynthesis imaging performed in the state where the subject is compressed in a second direction different from the first direction. For example, the specifying function 26b specifies a corresponding second tomogram that includes an area corresponding to the region or interest, from among multiple second tomograms acquired by imaging the breast in a second imaging direction different from the first imaging direction. In this example, the second direction is the second imaging direction, and the second imaging direction is the MLO direction. The specifying function 26b may specify the second tomogram based on the position of the region of interest, and the second direction. For example, the specifying function 26b may specify the corresponding second tomogram based on the position of the region of interest, the multiple second tomograms, and the second imaging direction. The specifying function 26b is one example of a specifier.

The skin-outline detecting function 26b1 detects the outline of skin from the tomogram that includes the designated region of interest. This skin outline is a curving line that draws the profile of the breast in the tomogram, and can be detected through, for example, threshold processing.

The breast-end determining function 26b2 determines, in the tomogram including the detected skin outline, one and the other ends of the breast drawn by the skin outline.

The coordinate calculating function 26b3 calculates coordinates of the region of interest on a schematic diagram that schematically expresses the breast. Here, the coordinate calculating function 26b3 determines, on this schematic diagram, a position of the region of interest in the direction orthogonal to the first imaging direction based on the one and the other ends of the breast in the tomogram as one of multiple first tomograms. This position in the direction orthogonal to the first imaging direction serves as the x-coordinate of the region of interest on the schematic diagram, and can be determined by calculating at what ratio the region of interest internally divides the segment from the one end to the other end of the breast. The coordinate calculating function 26b3 also determines, on the schematic diagram, a position of the region of interest in the first imaging direction based on the slice number assigned to said one of the first tomograms and the total number of the slices of the first tomograms. This position in the first imaging direction serves as the y-coordinate of the region of interest on the schematic diagram, and can be determined by calculating a ratio represented by the slice number with respect to the total number of slices.

The slice-number calculating function 26b4 specifies the corresponding second tomogram by locating, on the schematic diagram, an intersection between the imaging axis in the second imaging direction and a straight line orthogonal to this imaging axis and extending through the determined position (coordinates) of the region of interest. For example, the slice-number calculating function 26b4 calculates a slice number of the corresponding second tomogram based on the ratio at which the located intersection internally divides the imaging axis within the breast on the schematic diagram and based on the total number of the slices, so that the corresponding second tomogram assigned with this slice number is specified. As such, the slice-number calculating function 26b4 may be used as a function to specify the slice number of the corresponding second tomogram by calculating the slice number based on the ratio at which the located intersection internally divides the imaging axis within the breast on the schematic diagram and based on the total number of the slices.

The display control function 26c causes the display 27 to display the corresponding second tomogram specified by the specifying function 26b. The display control function 26c may cause the display 27 to display a still image of the corresponding second tomogram. Alternatively or additionally, the display control function 26c may cause the display 27 to display a moving image that includes the corresponding second tomogram and a predetermined number of second tomograms before and after the corresponding second tomogram. The display control function 26c may further cause the display 27 to display a moving image that includes the first tomogram concerned and a predetermined number of first tomograms before and after it, next to the display area for said predetermined number of the second tomograms. The display control function 26c is one example of a display controller.

The display 27 includes a display main part for displaying medical images, etc., internal circuitry for supplying signals for display to the display main part, and peripheral circuitry including connectors, cables, or the like for connection between the display main part and the internal circuitry. The display 27 is adapted to display the medical images, etc., under the control of the processing circuitry 26. For example, the display 27 displays tomograms generated by the image generating circuitry 25, the schematic diagram (body mark BM) generated by the processing circuitry 26, and so on. Also for example, the display 27 displays the first tomogram that includes the designated region of interest, and the corresponding second tomogram that includes an area corresponding to the region of interest among multiple second tomograms. The display 27 is one example of a display.

The system control circuitry 28 includes a processor and a memory (not illustrated), and serves as a center of the X-ray diagnostic apparatus 1 to control each component.

The network interface 29 is circuitry for connecting the computer device 5 to the network Nw for communications with entities or apparatuses such as the medical image processing apparatus 30. As the network interface 29, for example, a network interface card (NIC) may be adopted. The following description will omit such an explanation as the network interface 29 being present between the computer device 5 and the medical image processing apparatus 30 for communication.

Note that the computer device 5 and the X-ray imaging stand 3 may be provided as an integral unit.

On the other hand, the medical image processing apparatus 30 includes a memory 31, an input interface 32, a display 33, a network interface 34, and processing circuitry 35, as shown in FIG. 5.

The memory 31 is constituted by a memory main component for storing electric information, such as a ROM, a RAM, an HDD, an image memory, etc., as well as peripheral circuitry pertaining to the memory main component, such as a memory controller, a memory interface, etc. The memory 31 is adapted to store one or more medical images and programs. Examples of the medical images include mammograms acquired under normal imaging, and tomograms acquired under tomosynthesis imaging. For example, the memory 31 stores, in conjunction with tomosynthesis imaging, multiple first tomograms acquired by imaging the subject's breast in a first imaging direction, and multiple second tomograms acquired by imaging the breast in a second imaging direction different from the first imaging direction. This embodiment assumes the first imaging direction and the second imaging direction to be the CC direction and the MLO direction, respectively. The multiple tomograms are each assigned a slice number, and can accordingly be specified or identified by the assigned slice number. Particulars about the slice number are as described above. The first tomograms and the second tomograms may each include, for example, accessory information (not illustrated) containing corresponding imaging conditions, a code indicative of the imaging direction (imaging angle) used at the imaging, a code indicative of whether the imaged subject is the right breast or the left breast, and so on. The program stored in the memory 31 may cause a computer to implement, for example, a designating function and a specifying function. This designating function corresponds to a region-of-interest designating function 35a, which will be described later. The specifying function corresponds to a specifying function 35b, also described later. The specifying function 35b may include, for example, a skin-outline detecting function 35b1, a breast-end determining function 35b2, a coordinate calculating function 35b3, and a slice-number calculating function 35b4, as appropriate. The program may further cause the computer to implement a display control function. This display control function corresponds to a display control function 35c, described later. Additionally, such a program may be, for example, installed in the computer from the network or a non-transitory computer-readable storage medium M2 in advance, so that the computer will realize each function of the medical image processing apparatus 30. The program includes, for example, instructions for the processor of the computer to perform each function.

The input interface 32 is realized by components for an operator to input various instructions, commands, information, selections, settings, etc. to the medical image processing apparatus 30 itself, and such components include a trackball, switch buttons, a mouse, a keyboard, a touch pad which allows an input operation through contacting the operation screen, and a touch panel display which integrates a display screen and a touch pad. The input interface 32 is connected to the processing circuitry 35, and adapted to convert input operations received from the operator into electric signals and to output the electric signals to the processing circuitry 35. Note that, when the following explanation of the medical image processing apparatus 30 mentions "operator's operation", it may be taken as "operation on the input interface 32 by the operator". Also, in the disclosure herein, the input interface 32 is not limited to physical operating components such as a mouse and a keyboard. That is, the examples of the input interface 32 also include processing circuitry for electrical signals that is adapted to receive an electrical signal corresponding to an input operation from an external input device separate from the apparatus, and to output this electrical signal to the processing circuitry 35.

The display 33 includes a display main part for displaying medical images, etc., internal circuitry for supplying signals for display to the display main part, and peripheral circuitry including connectors, cables, or the like for connection between the display main part and the internal circuitry. The display 33 is adapted to display the medical images, etc., under the control of the processing circuitry 35. For example, the display 33 displays the first tomogram that includes the designated region of interest, and the corresponding second tomogram that includes an area corresponding to the region of interest among multiple second tomograms. The display 33 is another example of the display.

The network interface 34 is circuitry for connecting the medical image processing apparatus 30 to the network Nw for communications with entities or apparatuses such as the computer device 5. As the network interface 34, for example, a network interface card (NIC) may be adopted. The following description will omit such an explanation as the network interface 34 being present between the medical image processing apparatus 30 and the computer device 5, etc. for communication.

The processing circuitry 35 reads the tomograms with accessory information and also the program from the memory 31 according to an instruction input by the operator through the input interface 32, and controls the medical image processing apparatus 30 based on these. For example, the processing circuitry 35 is a processor to realize, in addition to existing functions, various functions for assisting the interpretation of medical images according to the program read from the memory 31. Such various functions include, for example, the aforementioned region-of-interest designating function 35a, specifying function 35b, and display control function 35c. The specifying function 35b may include, for example, a skin-outline detecting function 35b1, a breast-end determining function 35b2, a coordinate calculating function 35b3, and a slice-number calculating function 35b4, as appropriate. Note that the display control function 35c and the display 33 may be mounted on other computer (not illustrated), instead of the medical image processing apparatus 30. In such instances, for example, the medical image processing apparatus 30 may operate as a server device, and said other computer may operate as a client device that displays the second tomogram specified by the server device.

The region-of-interest designating function 35a designates a region of interest in a first tomogram among multiple tomograms which are based on tomosynthesis imaging performed in the state where the subject is compressed in a first direction. For example, the region-of-interest designating function 35a designates a region of interest in one of multiple first tomograms acquired by imaging the subject's breast in a first imaging direction. In this example, the first direction is the first imaging direction, and the first imaging direction is the CC direction. Also in this example, the "subject" as an imaging target is the "subject's breast" or a "breast". When the term "breast" appears without "subject's", it may be taken as "subject". Designating the region of interest may be performed according to an operation on the input interface 32 by the operator, or according to a result of detecting a pathological region through mammography CAD. The region-of-interest designating function 35a is another example of the designator.

The specifying function 35b specifies a second tomogram corresponding to the region of interest from among multiple tomograms which are based on tomosynthesis imaging performed in the state where the subject is compressed in a second direction different from the first direction. For example, the specifying function 35b specifies a corresponding second tomogram that includes an area corresponding to the region or interest, from among multiple second tomograms acquired by imaging the breast in a second imaging direction different from the first imaging direction. In this example, the second direction is the second imaging direction, and the second imaging direction is the MLO direction. The specifying function 35b may specify the second tomogram based on the position of the region of interest, and the second direction. For example, the specifying function 35b may specify the corresponding second tomogram based on the position of the region of interest, the multiple second tomograms, and the second imaging direction. The specifying function 35b is another example of the specifier.

The skin-outline detecting function 35b1 detects the outline of skin from the first tomogram that includes the designated region of interest. This skin outline is a curving line that draws the profile of the breast in the first tomogram, and can be detected through, for example, threshold processing.

The breast-end determining function 35b2 determines, in the first tomogram including the detected skin outline, one and the other ends of the breast drawn by the skin outline.

The coordinate calculating function 35b3 calculates coordinates of the region of interest on a schematic diagram that schematically expresses the breast. Here, the coordinate calculating function 35b3 determines, on this schematic diagram, a position of the region of interest in the direction orthogonal to the first imaging direction based on the one and the other ends of the breast in the first tomogram as one of multiple first tomograms. This position in the direction orthogonal to the first imaging direction serves as the x-coordinate of the region of interest on the schematic diagram, and can be determined by calculating at what ratio the region of interest internally divides the segment from the one end to the other end of the breast. The coordinate calculating function 35b3 also determines, on the schematic diagram, a position of the region of interest in the first imaging direction based on the slice number assigned to said one of the first tomograms and the total number of the slices of the first tomograms. This position in the first imaging direction serves as the y-coordinate of the region of interest on the schematic diagram, and can be determined by calculating a ratio represented by the slice number with respect to the total number of slices.

The slice-number calculating function 35b4 specifies the corresponding second tomogram by locating, on the schematic diagram, an intersection between the imaging axis in the second imaging direction and a straight line orthogonal to this imaging axis and extending through the determined position (coordinates) of the region of interest. For example, the slice-number calculating function 35b4 calculates a slice number of the corresponding second tomogram based on the ratio at which the located intersection internally divides the imaging axis within the breast on the schematic diagram and based on the total number of the slices, so that the corresponding second tomogram assigned with this slice number is specified. As such, the slice-number calculating function 35b4 may be used as a function to specify the slice number of the corresponding second tomogram by calculating the slice number based on the ratio at which the located intersection internally divides the imaging axis within the breast on the schematic diagram and based on the total number of the slices.

The display control function 35c causes the display 33 to display the corresponding second tomogram specified by the specifying function 35b. The display control function 35c may cause the display 33 to display a still image of the corresponding second tomogram. Alternatively or additionally, the display control function 35c may cause the display 33 to display a moving image that includes the corresponding second tomogram and a predetermined number of second tomograms before and after the corresponding second tomogram. The display control function 35c may further cause the display 33 to display a moving image that includes the first tomogram concerned and a predetermined number of first tomograms before and after it, next to the display area for said predetermined number of the second tomograms. The display control function 35c is another example of the display controller.

Now, how the medical image processing apparatus 30 configured as above operates will be described with reference to FIGS. 6 to 17. Note that the processing circuitry 26 of the X-ray diagnostic apparatus 1 and the processing circuitry 35 of the medical image processing apparatus 30 are adapted to operate in substantially the same manner for the exemplary functions discussed above, namely, the region-of-interest designating function 26a;35a, the specifying function 26b;35b (the skin-outline detecting function 26b1;35b1, the breast-end determining function 26b2;35b2, the coordinate calculating function 26b3;35b3, and the slice-number calculating function 26b4;35b4), and the display control function 26c;35c. Thus, in order to avoid very redundant languages and to facilitate the understanding, the following description about the operations of the respective functions will assume, as a representative example, the case with the processing circuitry 35 of the medical image processing apparatus 30. The description of the representative example as such can be applied to the operations of the processing circuitry 26 of the X-ray diagnostic apparatus 1, upon appropriately replacing the apparatus name, reference symbols, etc. Note that the "schematic diagram that schematically expresses the breast" in the preceding description may also be called a "body mark BM".

Suppose that, as step ST10, the X-ray diagnostic apparatus 1 has now performed tomosynthesis imaging on the breast of a subject and written the acquired tomograms in the memory 22. Accordingly, the memory 22 in the X-ray diagnostic apparatus 1 stores multiple first tomograms acquired by imaging the subject's breast in the CC direction and multiple second tomograms acquired by imaging the breast in the MLO direction different from the CC direction.

It is also supposed that, in this step, the medical image processing apparatus 30 has obtained the multiple first tomograms and the multiple second tomograms from the memory 22 in the X-ray diagnostic apparatus 1, for each examination of the subject's breast as per the operator's operation. The medical image processing apparatus 30 writes the obtained first tomograms and second tomograms in the memory 31. Thus, the memory 31 in the medical image processing apparatus 30 stores the multiple first tomograms acquired by imaging the subject's breast in the CC direction and the multiple second tomograms acquired by imaging the breast in the MLO direction different from the CC direction. Step ST10 is complete then.

In step ST20 after step ST10, the processing circuitry 35 of the medical image processing apparatus 30 causes the display 33 to display, as shown in the left portion of FIG. 7, the multiple first tomograms denoted here by VD_cc in accordance with, for example, an operation on the input interface 32 by the operator. The multiple first tomograms VD_cc include, for example, 40 first tomograms g_cc(#1) to g_cc(#40) each acquired by imaging the subject's right breast in the CC direction. The processing circuitry 35 also designates a region of interest r_cc in, for example, one first tomogram g_cc(#20) of the multiple first tomograms VD_cc in accordance with the operator's operation. Step ST20 is thus complete.

After step ST20, step ST30 is performed where the processing circuitry 35 specifies, for example, a corresponding second tomogram g_mlo(#10) that includes an area r_mlo corresponding to the region of interest r_cc, from among multiple second tomograms VD_mlo acquired by imaging the subject's right breast in the MLO direction different from the CC direction. The multiple second tomograms VD_mlo include, for example, 40 second tomograms g_mlo(#1) to g_mlo(#40) each acquired by imaging the subject's right breast in the MLO direction. More concretely, and for example, the processing circuitry 35 specifies the corresponding second tomogram g_mlo(#10) based on the position of the region of interest r_cc, the multiple second tomograms VD_mlo, and the MLO direction. Performing this step ST30 proceeds with, for example, steps ST31 to ST37 as will be described with reference to FIGS. 7 to 11.

In step ST31, the processing circuitry 35 detects the outline of skin from the first tomogram g_cc(#20) that includes the designated region of interest r_cc as shown in the left portion of FIG. 7. This skin outline can be detected as a boundary between the breast region and the space region through, for example, threshold processing where each pixel of the first tomogram g_cc(#20) is compared to a given threshold. Step ST31 is thus complete.

After step ST31, step ST32 is performed where the processing circuitry 35 determines, in the first tomogram g_cc(#20) including the detected skin outline, one and the other ends of the breast drawn by the skin outline. More concretely, and for example, the one and the other ends of the breast are each determined from the skin outline on the chest wall side of the first tomogram g_cc(#20). Step ST32 is thus complete.

After step ST32, step ST33 is performed where the processing circuitry 35 calculates the coordinate of the region of interest r_cc on a body mark BM schematically expressing the subject's right breast as shown in the right portion of FIG. 7. This body mark BM contains a circular graph representing the breast, X- and Y-coordinate axes dividing the circular graph into first to fourth quadrants (with the Y-axis being a vertical axis and the X-axis being a horizontal axis), and a triangle-like shape stretching up and leftward from the arc of the second quadrant. This triangle-like shape represents the subject's right armpit. The origin of the XY coordinates represents the nipple. For example, the circular graph has a radius of 1 and a diameter of 2. Thus, in the body mark BM in this case, the origin has coordinates (0, 0), the highest point has coordinates (0, 1), and the lowest point has coordinates (0, −1). In the body mark BM, the right-most point has coordinates (1, 0), and the left-most point has coordinates (−1, 0). The line at the top of the circular graph and parallel to the horizontal axis corresponds to the 1st one of the first tomograms, i.e., first tomogram g_cc(#1), and the line overlapping the horizontal axis corresponds to the 20th one of the first tomograms, i.e., first tomogram g_cc(#20). Since, in the body mark BM shown in FIG. 7, the line overlapping the horizontal axis of the circular graph extends through the coordinate origin (nipple), the first tomogram g_cc(#20) is an image that captures the nipple as illustrated in the left portion of FIG. 7. The line at the bottom of the circular graph and parallel to the horizontal axis corresponds to the 40th one of the first tomograms, i.e., first tomogram g_cc(#40).

Here, the processing circuitry 35 determines, on the body mark BM, a position of the region of interest r_cc in the direction (width direction) orthogonal to the CC direction, based on the one and the other ends of the breast in the first tomogram g_cc(#20). This position in the width direction is the x-coordinate of the region of interest r_cc on the body mark BM, and is determined by calculating a ratio a:b at which the region of interest r_cc internally divides the segment from the one end to the other end of the breast in the first tomogram g_cc(#20). In other words, the ratio a:b obtained based on the first tomogram g_cc(#20) can be applied to the body mark BM for the width direction so that the x-coordinate of the region of interest r_cc on the body mark BM is determined. As an example of obtaining this x-coordinate, when the ratio a:b in FIG. 7 is 3:1, then x=0.5 because a:b=(x−(−1)):(1−x). As another example, when the ratio a:b is 7:3, then x=0.4 and the x-coordinate has thus been similarly obtained. Note that said equation uses the negative x-coordinate "−1" and the positive x-coordinate "1" for the circle of the body mark BM for the first tomogram g_cc(#20), and these coordinates are on the X-axis, i.e., the horizontal axis, since the first tomogram g_cc(#20) is at the midpoint among the total slice number "40". However, the negative x-coordinate and the positive x-coordinate for the circle of the body mark BM, used in the above equation, may also be obtained by substituting the y-coordinate determined in below step ST34 for the value in the circle's equation $x^2+y^2=1^2$ (where the symbol "^" indicates exponentiation). In any case, step ST33 is complete upon determining the x-coordinate.

Figure 8:
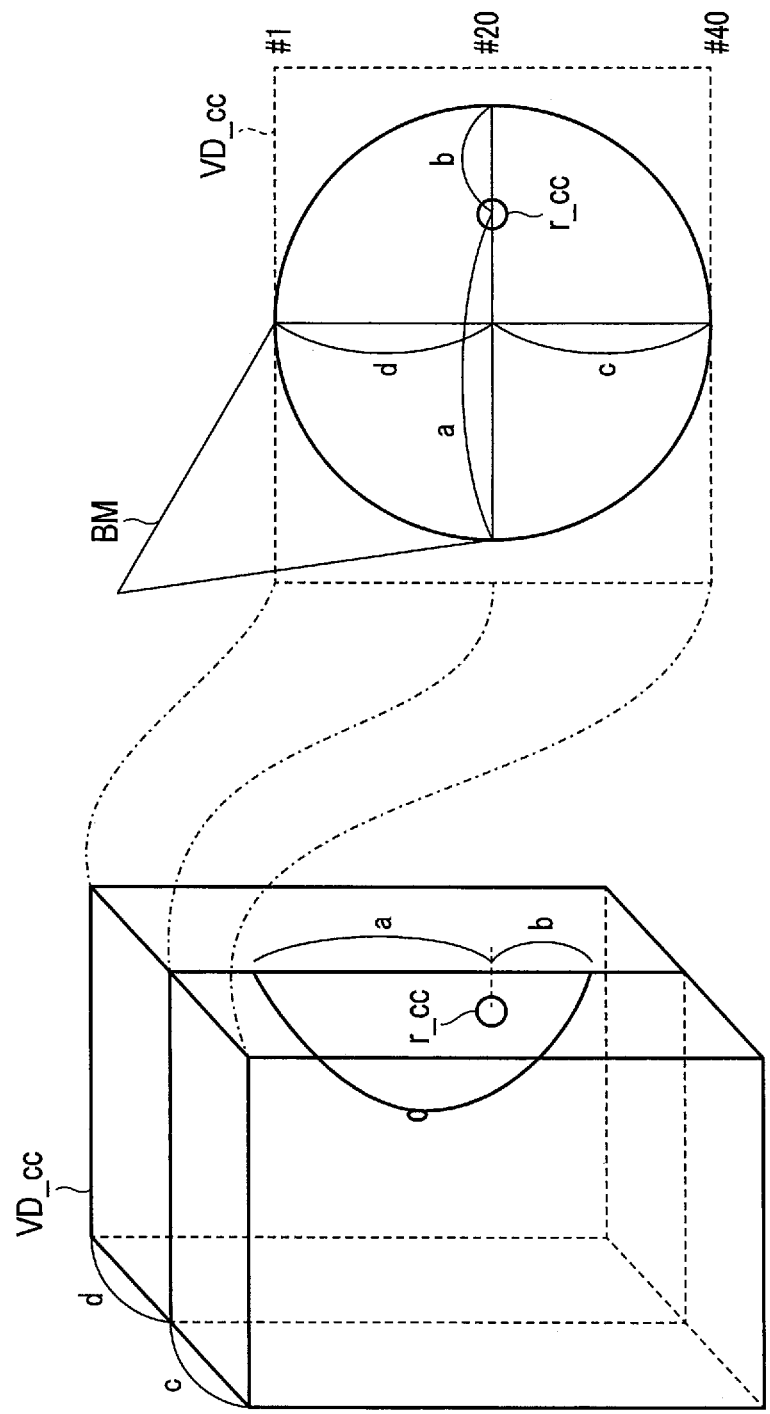
FIG. 8 is a diagram for explaining an exemplary operation according to the embodiment.
Figure 9:
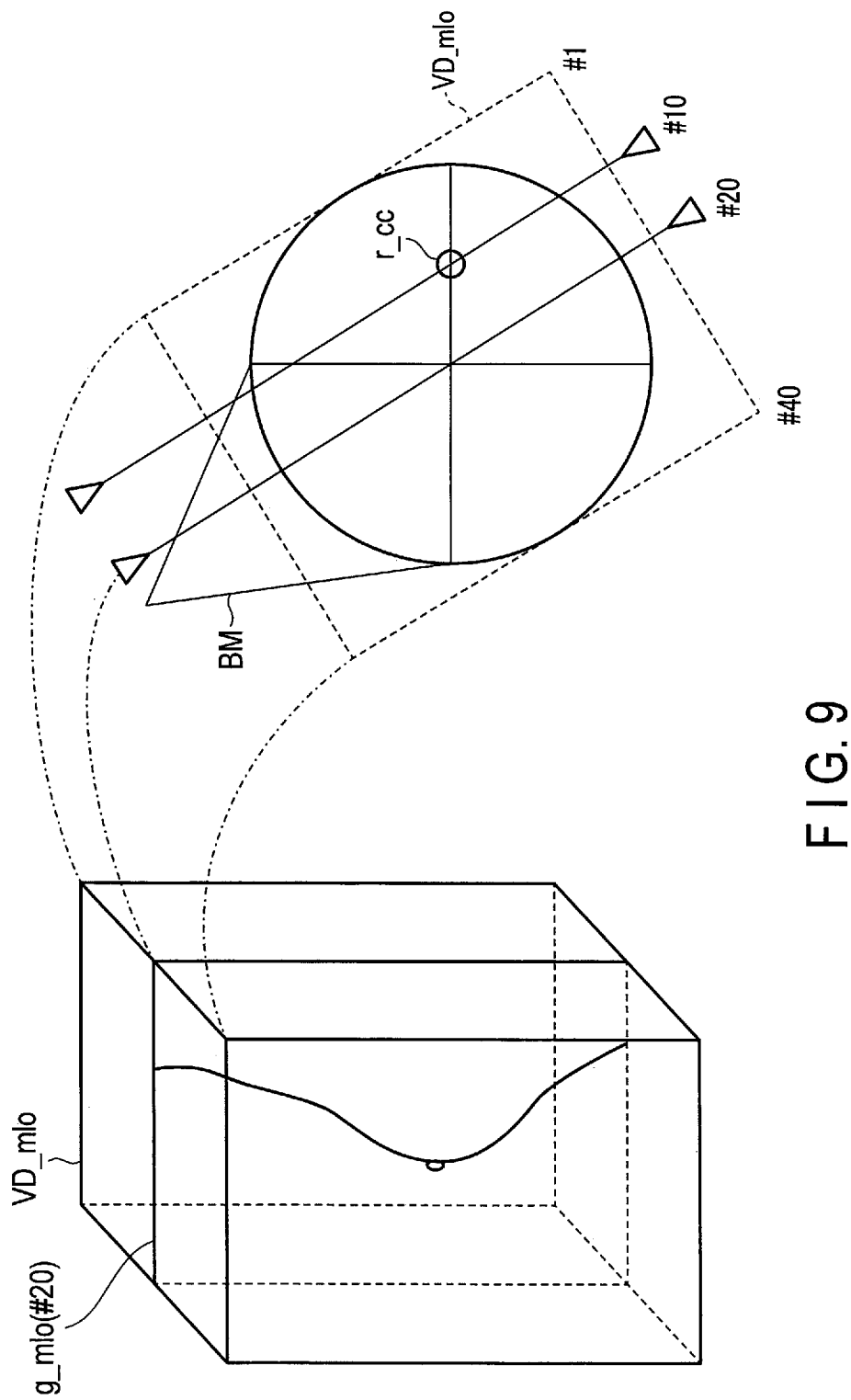
FIG. 9 is a diagram showing one example of a tomogram and a body mark upon performing tomosynthesis imaging for the subject's right breast in the MLO direction in the context of the embodiment.

After step ST33, step ST34 is performed where the processing circuitry 35 determines, on the body mark BM, a position of the region of interest r_cc in the CC direction, based on the slice number "#20" indicative of the first tomogram g_cc(#20) and the total number "40" of the slices of the first tomograms VD_cc as shown in FIG. 8. This position in the CC direction is the y-coordinate of the region of interest r_cc on the body mark BM, and is determined by calculating a value d=20/40 for the ratio of the slice number "#20" with respect to the total slice number "40", and calculating the remaining value c=1−d for the ratio. In other words, the ratio d:c obtained based on the slice number of the first tomogram g_cc(#20) can be applied to the body mark BM for the vertical axis direction so that the y-coordinate of the region of interest r_cc on the body mark BM is determined. For example, since d=0.5 and c=0.5 in FIG. 8, d:c is 1:1. Because d:c=(1−y):(y−(−1)), the y-coordinate is obtained as y=0. In this equation, the positive y-coordinate "1" and the negative y-coordinate "−1" for the circle of the body mark BM are invariables. Step ST34 is thus complete. Note that steps ST33 and ST34 may be performed in reverse order.

Figure 10:
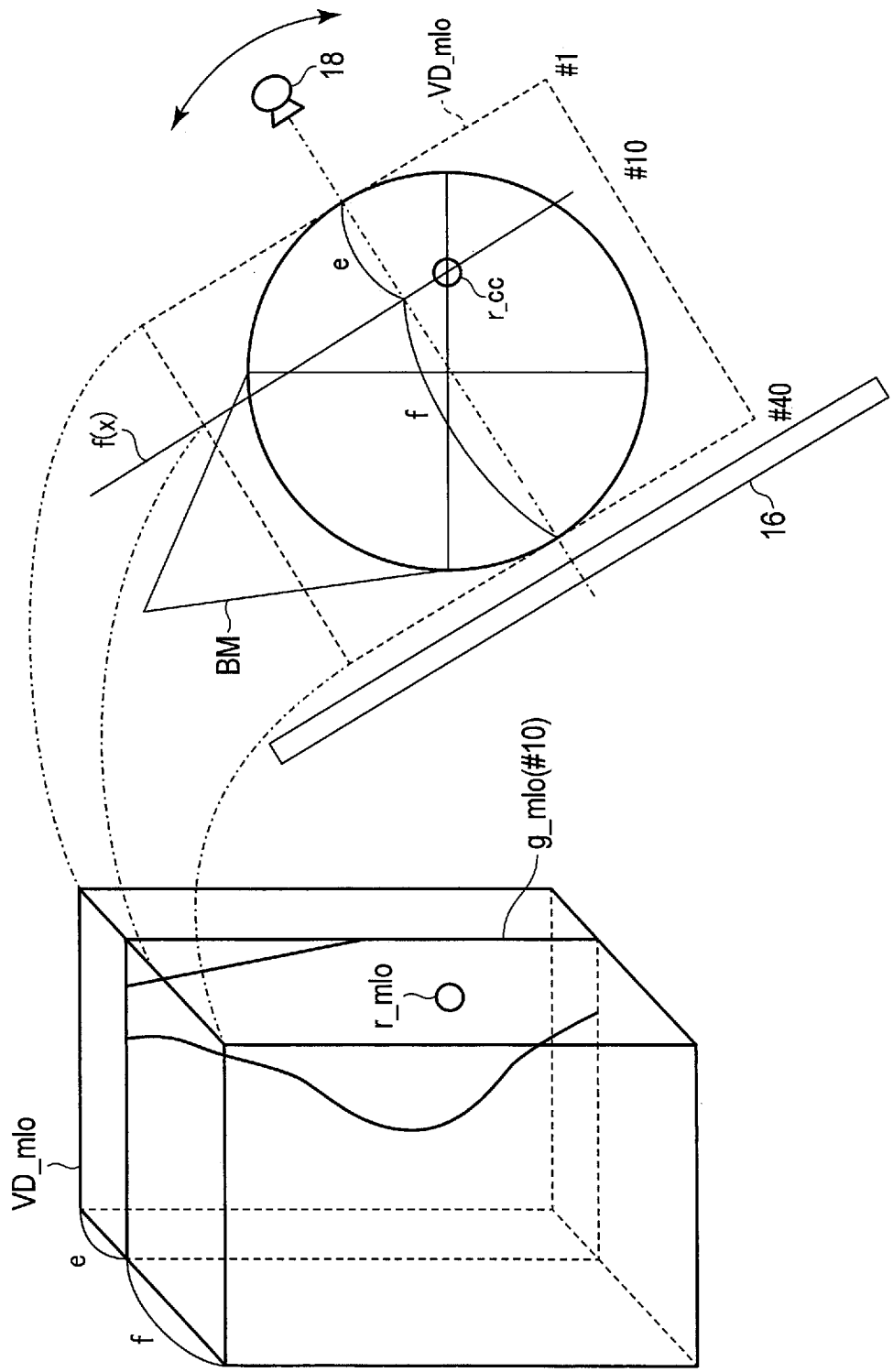
FIG. 10 is a diagram for explaining an exemplary operation according to the embodiment.
Figure 12:
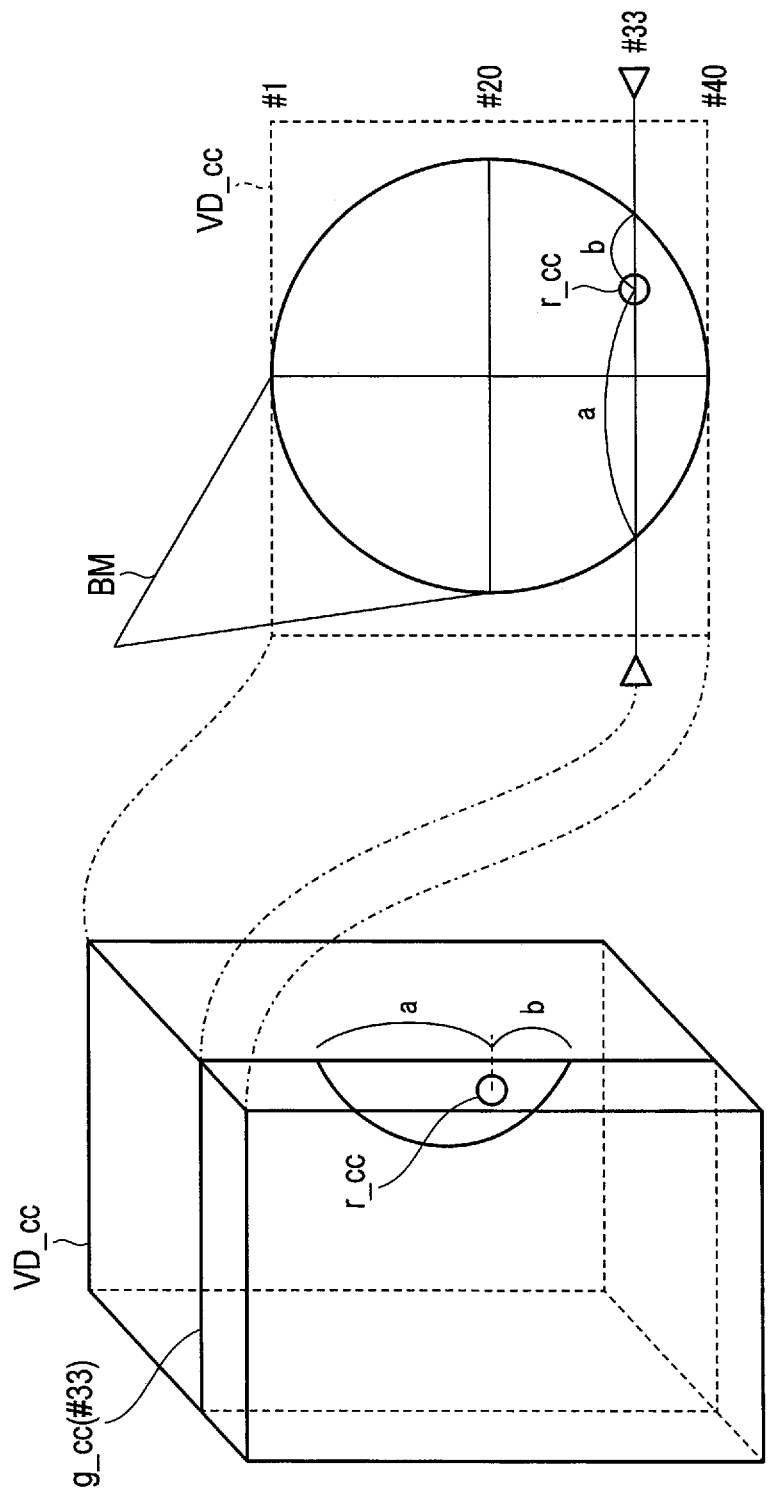
FIG. 12 is a diagram showing another example of a tomogram and a body mark upon performing tomosynthesis imaging for the subject's right breast in the CC direction in the context of the embodiment.
Figure 13:
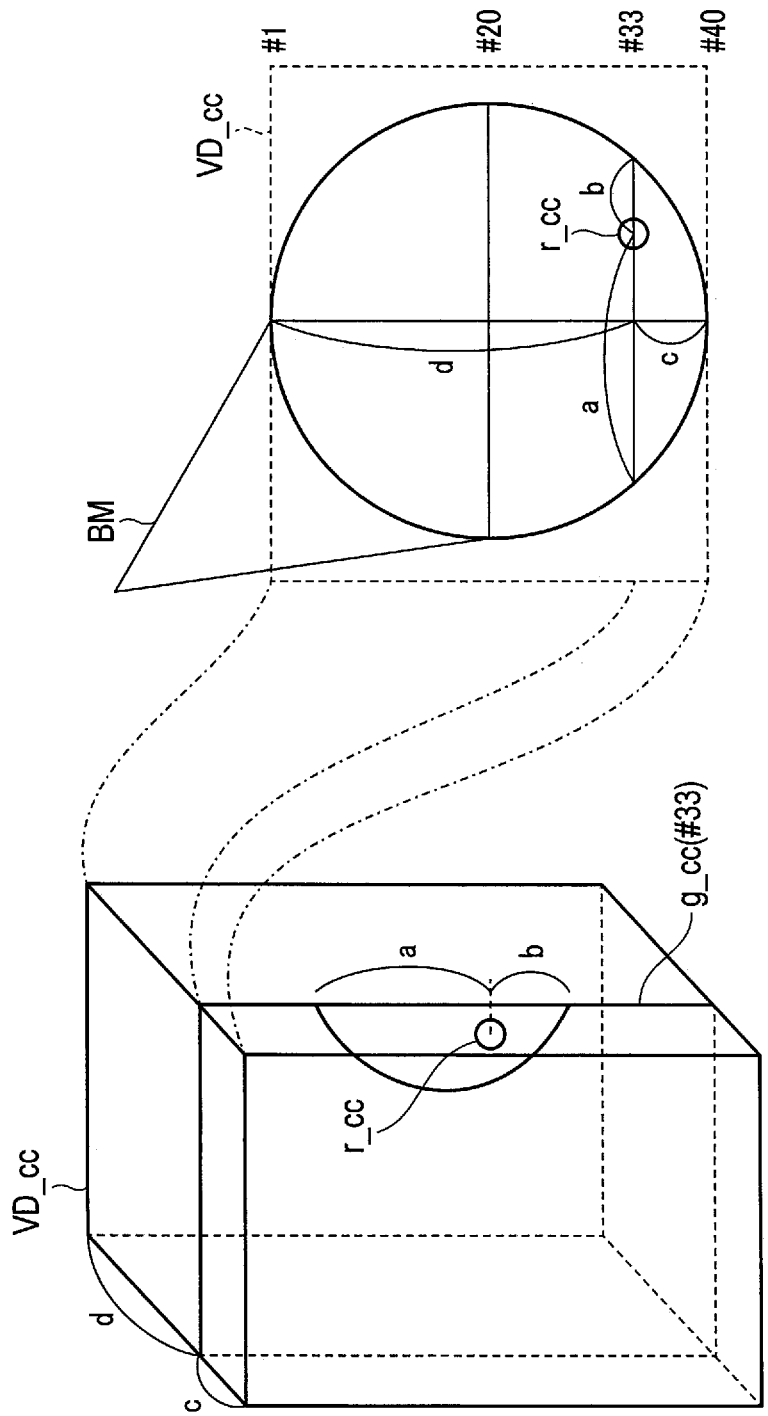
FIG. 13 is a diagram for explaining another exemplary operation according to the embodiment.
Figure 14:
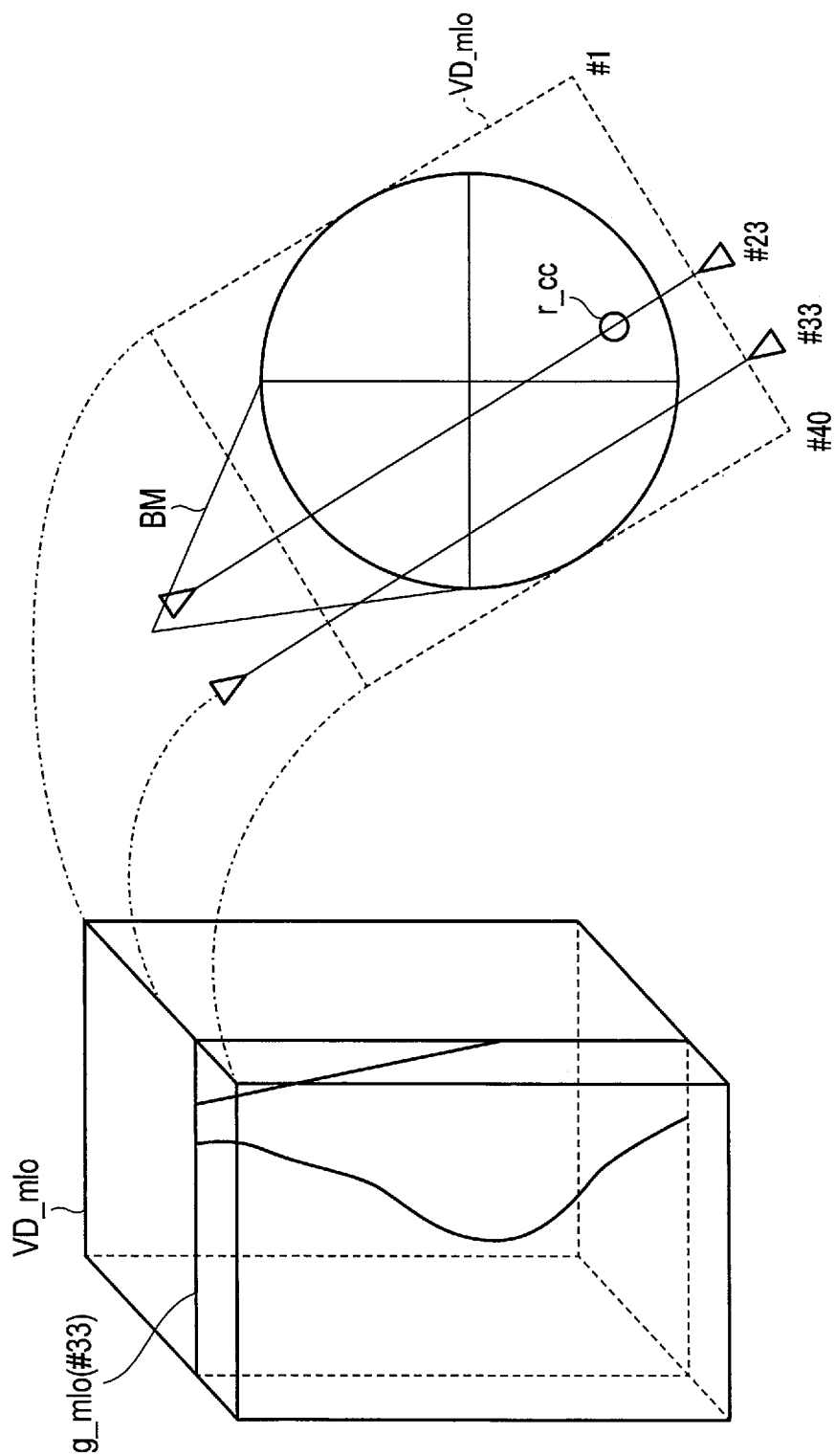
FIG. 14 is a diagram showing another example of a tomogram and a body mark upon performing tomosynthesis imaging for the subject's right breast in the MLO direction in the context of the embodiment.
Figure 16:
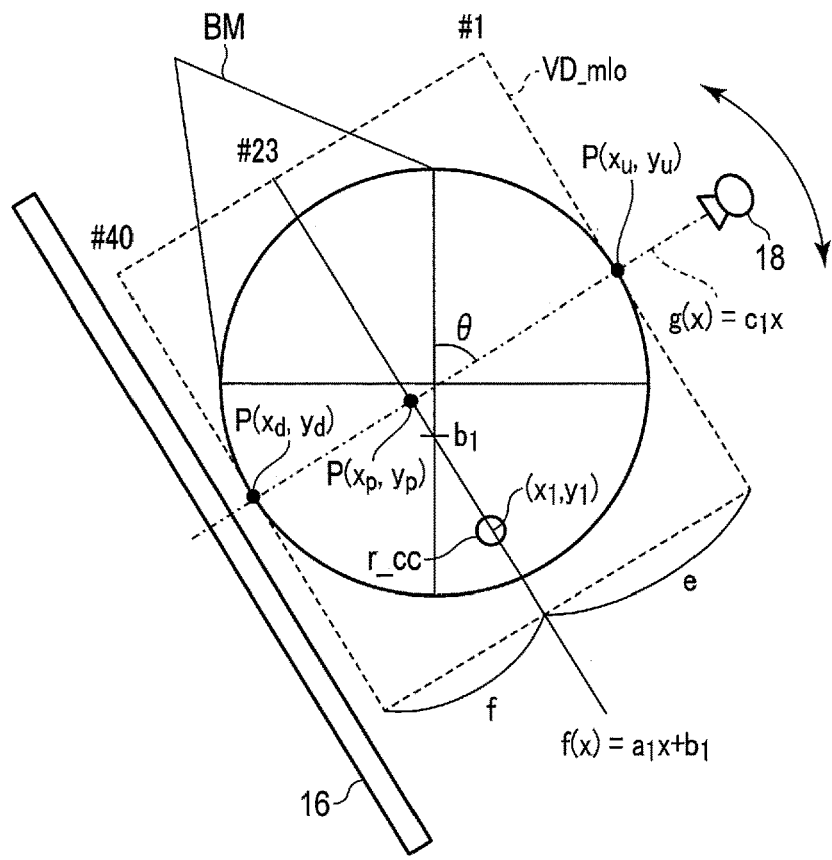
FIG. 16 is a diagram for explaining another exemplary operation according to the embodiment.

Subsequent to step ST34, the processing circuitry 35 will locate, on the body mark BM, the intersection between the imaging axis in the MLO direction and a straight line orthogonal to this imaging axis and extending through the determined position (coordinates) of the region of interest r_cc (step ST35), so as to specify the corresponding second tomogram g_mlo(#i) (steps ST36 to ST37). To be more specific, the MLO direction-based second tomogram g_mlo (#20), which has the same slice number "#20" as the first tomogram g_cc(#20) including the region of interest r_cc as shown in FIG. 7, does not include an area corresponding to the region of interest r_cc as can be seen from FIG. 9. Meanwhile, as shown in FIG. 10, the tomogram that includes an area r_mlo corresponding to the region of interest r_cc, for example, the second tomogram g_mlo (#10), conforms to a straight line f(x) that extends through the position of the region of interest r_cc while being orthogonal to the imaging axis in the MLO direction on the body mark BM. Accordingly, step ST35 is employed in order to find out the straight line f(x).

In step ST35, the processing circuitry 35 locates, on the body mark BM, the intersection P $(x_p, y_p)$ between the imaging axis g(x) in the MLO direction and the straight line f(x) extending through the determined position of the region of interest r_cc and orthogonal to the imaging axis g(x) as shown in FIG. 11. Here, the imaging axis g(x) is a straight line extending through the origin, and can be given as $g(x)=c_1 \cdot x$. The inclination $c_1$ is obtained from the imaging angle θ representing the MLO direction. Also, the straight line f(x) can be given as $f(x)=a_1 \cdot x+b_1$. The inclination $a_1$ is obtained from the imaging angle θ representing the MLO direction. The y-intercept $b_1$ is obtained from the inclination $a_1$ and the coordinates $(x_1, y_1)$ of the region of interest r_cc. As such, the x-coordinate $x_p$ of the intersection P can be obtained as $c_1 \cdot x=a_1 \cdot x+b_1$, assuming that g(x)=f(x). The y-coordinate $y_p$ of the intersection P can be obtained as $y_p=c_1 \cdot x_p$, based on the x-coordinate $x_p$ of the intersection P and the imaging axis g(x). Step ST35 is thus complete.

After this step ST35, step ST36 is performed where the processing circuitry 35 calculates a ratio e:f at which the intersection P $(x_p, y_p)$, obtained in step ST35, internally divides the imaging axis g(x) within the breast on the body mark BM. The length of the portion e can be given as $1-(x_p^2+y_p^2)^{1/2}$. The length of the portion f can be given as $1+(x_p^2+y_p^2)^{1/2}$. Accordingly, the ratio e:f for the internal division is obtained.

Calculations of the e and f lengths are not limited to this, and may also be performed differently, for example, in the following manner. For the e length, one of the two intersections between the circle of the body mark BM and the imaging axis g(x) shown in FIG. 11, namely, the intersection P $(x_u, y_u)$ on the side of the breast's upper end, is calculated. Based on the imaging angle θ, the x-coordinate $x_u$ and the y-coordinate $y_u$ of this intersection P are obtained as $x_u=\cos(90°-θ)$ and $y_u=\sin(90°-θ)$, respectively. The formula for trigonometric function may discretionarily be altered. The e length may also be calculated as $e=\{(x_u-x_p)^2+(y_u-y_p)^2\}^{1/2}$.

Similarly, for the f length, the other one of the two intersections between the circle of the body mark BM and the imaging axis g(x) shown in FIG. 11, namely, the intersection P $(x_d, y_d)$ on the side of the breast's lower end, is calculated. Based on the imaging angle θ, the x-coordinate $x_d$ and the y-coordinate $y_d$ of this intersection P are obtained as $x_d=\cos(270°-θ)$ and $y_d=\sin(270°-θ)$, respectively. The formula for trigonometric function may discretionarily be altered. The f length may also be calculated as $f=\{(x_p-x_d)^2+(y_p-y_d)^2\}^{1/2}$. In any case, step ST36 is complete upon obtaining the ratio e:f for the internal division.

After step ST36, step ST37 is performed where the processing circuitry 35 specifies the corresponding second tomogram based on the ratio at which the intersection obtained in step ST35 internally divides the imaging axis within the breast on the body mark BM, and based on the total number of the slices. To be more specific, the processing circuitry 35 specifies the corresponding second tomogram g_mlo(#i) by calculating its slice number #i based on the internal division ratio e:f and the total slice number "40". The slice number #i here can be calculated as i=e/(e+f)× (total slice number). For example, when e=0.5 and f=1.5, #i is calculated to be #10, because i=0.5/(0.5+1.5)×40=10. Accordingly, the processing circuitry 35 specifies the MLO direction-based second tomogram g_mlo(#10) having a slice number equal to the calculated #10, as the corresponding second tomogram. Step ST37 is complete. Step ST30, including steps ST31 to ST37 as described above with reference to FIGS. 7 to 11, is thus complete. Note that the example illustrated with FIGS. 7 to 11 involves the region of interest r_cc that is exactly on the X-axis, i.e., the horizontal axis, so the calculations described for this example have been simple. However, application of step ST30 is not limited to such an example. Step ST30 is also applicable to the instances where the region of interest r_cc is not on the X-axis in the body mark BM as shown in, for example, FIGS. 12 to 16, and steps ST31 to ST37 in such instances can be performed in a similar manner while reversing the order of steps ST33 and ST34. In any case, step ST30 is complete upon performing steps ST31 to ST37.

Figure 17:
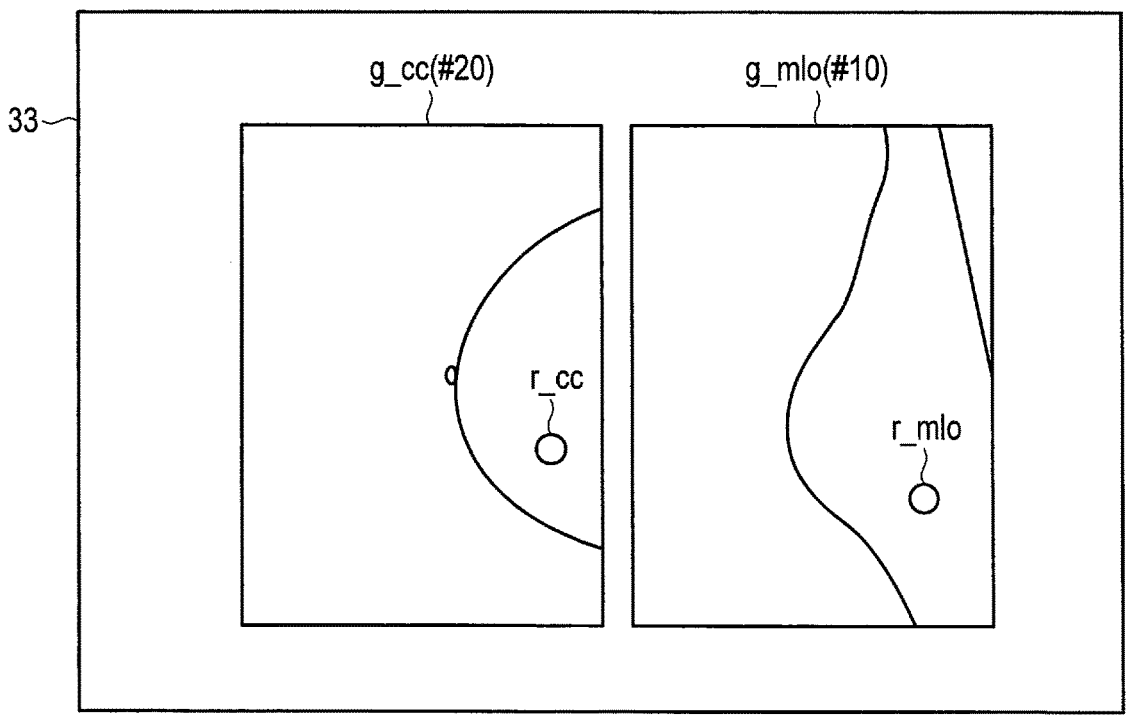
FIG. 17 is a diagram for explaining an exemplary operation according to the embodiment.

In step ST40 after step ST30, the processing circuitry 35 causes the display 33 to display the first tomogram g_cc (#20) with the designated region of interest r_cc and the specified corresponding second tomogram g_mlo(#10) in the manner as shown in, for example, FIG. 17. The corresponding second tomogram g_mlo(#10) includes the area r_mlo corresponding to the region of interest r_cc. Therefore, the operator, etc. can perform diagnostic interpretation with the MLO direction-based second tomogram g_mlo (#10) that corresponds to the region of interest r_cc in the CC direction-based first tomogram r_cc(#20) for the subject's right breast. When the subject's left breast has already undergone the tomosynthesis imaging, performing steps ST20 to ST40 in the above manner can likewise allow for the interpretation for the breast.

According to a certain embodiment as described, a region of interest is designated in one of multiple first tomograms acquired by imaging the breast of a subject in a first imaging direction. A corresponding second tomogram that includes an area corresponding to the region or interest is specified from among multiple second tomograms acquired by imaging the breast in a second imaging direction different from the first imaging direction. More specifically, the corresponding second tomogram is specified based on the position of the region of interest, the multiple second tomograms, and the second imaging direction. In this manner, the embodiment achieves, beyond the conventional art, an advantageous configuration where only designating a region of interest in the first tomograms acquired in one imaging direction allows for specifying which of the second tomograms acquired in another imaging direction corresponds to the region of interest.

Also, according to the embodiment, only upon an interpreting doctor's designating a region of interest in a first tomogram acquired by tomosynthesis imaging at one angle, then the second tomogram corresponding to such a region of interest designated previously, among second tomograms acquired by tomosynthesis imaging at different angles, can be presented through a display. Therefore, as the second tomogram corresponding to the region of interest is made available without requiring the interpreting doctor to search for it, the interpreting doctor can spend less time for tomosynthesis interpretation.

According to the embodiment, a position of a region of interest in the direction orthogonal to the first imaging direction is determined on a schematic diagram schematically expressing the breast, based on one and the other ends of the breast in one first tomogram. Thus, the embodiment can, for example, reduce the load of calculation processing by employing such a simple calculation as determining the position of the region of interest between the one and the other ends of the breast in the orthogonal direction on the schematic diagram, without necessarily using the coordinates of the nipple.

Moreover, according to the embodiment, a position of the region of interest in the first imaging direction is determined on the schematic diagram, based on a slice number indicative of said one first tomogram and the total number of slices of the first tomograms. Thus, it is possible to determine the position of the region of interest on the schematic diagram by, for example, such a simple computation as setting a position represented by the slice number normalized with the total slice number to the y-coordinate, while omitting the operation by an operator.

According to the embodiment, the corresponding second tomogram is specified by locating, on the schematic diagram, an intersection between the imaging axis in the second imaging direction and a straight line orthogonal to this imaging axis and extending through the determined position of the region of interest. As such, the intersection between the imaging axis and the straight line extending through the position of the region of interest is obtained based on geometric relationships on the schematic diagram, and therefore, the embodiment allows the corresponding second tomogram to be specified by such a simple calculation as locating an intersection between two straight lines.

Moreover, according to the embodiment, a slice number assigned to the corresponding second tomogram is calculated based on a ratio at which the located intersection internally divides the imaging axis within the breast on the schematic diagram and based on the total number of the slices, so that the corresponding second tomogram is specified. Thus, it is possible to determine the position of the region of interest on the schematic diagram by, for example, such a simple calculation as identifying the slice number that internally divides the total number of the slices in concordance with the ratio for the internal division of the imaging axis.

According to the embodiment, furthermore, a display unit is caused to present the specified corresponding second tomogram so that, in addition to the effects as discussed, the operator, etc. can enjoy the advantage of conducting diagnostic interpretation with the use of the second tomogram specified in accordance with the region of interest in the first tomogram.

[Modifications]

Description will be given of modifications of the foregoing embodiment. The description will basically omit portions overlapping the foregoing embodiment, and concentrate on portions constituting differences. Any remaining embodiments, modifications, etc. will be set forth in the same manner. Also note that the first modification of the foregoing embodiment, which will be described next, is applicable also to the later-described second modification and third modification.

[First Modification]

The first modification relates to the instances where the first imaging direction is the MLO direction and the second imaging direction is the CC direction, unlike in the foregoing embodiment that has adopted the CC direction and the MLO direction as its respective first and second imaging directions.

According to this first modification, the X-ray diagnostic apparatus 1 and the medical image processing apparatus 30 include configurations similar to those described for the foregoing embodiment.

Now, how the medical image processing apparatus 30 of such configuration operates will be described using the flowchart of FIG. 6 again, as well as new FIGS. 18 to 22, etc.

Suppose that, as step ST10, the X-ray diagnostic apparatus 1 has now performed tomosynthesis imaging on the breast of a subject and written the acquired tomograms in the memory 22. Accordingly, the memory 22 in the X-ray diagnostic apparatus 1 stores multiple first tomograms acquired by imaging the subject's breast in the MLO direction and multiple second tomograms acquired by imaging the breast in the CC direction different from the MLO direction.

It is also supposed that, in this step, the medical image processing apparatus 30 has obtained the multiple first tomograms and the multiple second tomograms from the memory 22 in the X-ray diagnostic apparatus 1, for each examination of the subject's breast as per the operator's operation. The medical image processing apparatus 30 writes the obtained first tomograms and second tomograms in the memory 31. Thus, the memory 31 in the medical image processing apparatus 30 stores the multiple first tomograms acquired by imaging the subject's breast in the MLO direction and the multiple second tomograms acquired by imaging the breast in the CC direction. Upon this, step ST10 is complete.

In step ST20 after step ST10, the processing circuitry 35 of the medical image processing apparatus 30 causes the display 33 to display, as shown in the left portion of FIG. 18, the multiple first tomograms VD_mlo in accordance with, for example, an operation on the input interface 32 by the operator. Here, the multiple first tomograms VD_mlo include, for example, 40 first tomograms g_mlo(#1) to g_mlo(#40) each acquired by imaging the subject's right breast in the MLO direction. The processing circuitry 35 also designates a region of interest r_mlo in, for example, one first tomogram g_mlo(#23) of the multiple first tomograms VD_mlo in accordance with the operator's operation. Step ST20 is thus complete.

After step ST20, step ST30 is performed where the processing circuitry 35 specifies, for example, a corresponding second tomogram g_cc(#33) that includes an area r_cc corresponding to the region of interest r_mlo, from among multiple second tomograms VD_cc acquired by imaging the subject's right breast in the CC direction different from the MLO direction. The multiple second tomograms VD_cc include, for example, 40 second tomograms g_cc(#1) to g_cc(#40) each acquired by imaging the subject's right breast in the CC direction. More concretely, and for example, the processing circuitry 35 specifies the corresponding second tomogram g_cc(#33) based on the position of the region of interest r_mlo, the multiple second tomograms VD_cc, and the CC direction. Performing step ST30 of the first modification proceeds with, for example, steps ST31 to ST37 as will be described with reference to FIGS. 18 to 22.

In step ST31, the processing circuitry 35 detects the outline of skin from the first tomogram g_mlo(#23) that includes the designated region of interest r_mlo as shown in the left portion of FIG. 18. Step ST31 is then complete.

After step ST31, step ST32 is performed where the processing circuitry 35 determines, in the first tomogram g_mlo(#23) including the detected skin outline, one and the other ends of the breast drawn by the skin outline. The concrete manner of doing this includes, for example, drawing a straight line that connects the lower- and left-most pixel and the lower- and right-most pixel in the breast region, letting this straight line make a parallel translation from the region outside the breast region, and adopting, as the breast's lower end, a point of the skin outline in the first tomogram g_mlo(#23) that first touches the shifted straight line. Also, the breast's upper end is determined to be a point that is located above (in the y direction) the height of the nipple at a distance as much as the distance between this lower end of the breast and the height of the nipple in the y direction. The one and the other ends of the breast are thereby determined. Step ST32 is thus complete.

After step ST32, step ST33 is performed where the processing circuitry 35 calculates the coordinate of the region of interest r_mlo on a body mark BM schematically expressing the subject's right breast as shown in the right portion of FIG. 18. This body mark BM may be described similarly to the one employed in the foregoing embodiment. However, since the imaging direction for the first tomograms differs from that in the foregoing embodiment, some additional explanations will be given. The line at the top of the circular graph and orthogonal to the MLO direction-imaging axis corresponds to the 1st one of the first tomograms, i.e., first tomogram g_mlo(#1), and the parallel line crossing the circular graph at the applicable part and orthogonal to the imaging axis corresponds to the 23rd one of the first tomograms, i.e., first tomogram g_mlo(#23). Since, in the body mark BM shown in FIG. 18, the straight line corresponding to the first tomogram g_mlo(#23) does not extend through the coordinate origin (nipple), the first tomogram g_cc(#23) is an image that does not capture the nipple as illustrated in the left portion of FIG. 18. The line at the bottom of the circular graph and orthogonal to the imaging axis corresponds to the 40th one of the first tomograms, i.e., first tomogram g_mlo(#40).

Here, the processing circuitry 35 determines, on the body mark BM, a position of the region of interest r_mlo in the direction (right- and downwardly inclining direction) orthogonal to the MLO direction, based on the one and the other ends of the breast in the first tomogram g_mlo(#23). This position in the right- and downwardly inclining direction is the x-coordinate of the region of interest r_mlo on the body mark BM, and is determined by calculating a ratio a:b at which the region of interest r_mlo internally divides the segment from the one end to the other end of the breast in the first tomogram g_mlo(#23). In other words, the ratio a:b obtained based on the first tomogram g_mlo(#23) can be applied to the body mark BM for the right- and downwardly inclining direction so that the x-coordinate of the region of interest r_mlo on the body mark BM is determined. As discussed previously, the negative x-coordinate and the positive x-coordinate for the circle of the body mark BM may also be obtained by substituting the y-coordinate determined in below step ST34 for the value in the circle's equation $x^2+y^2=1^2$. In any case, step ST33 is complete upon determining the x-coordinate.

After step ST33, step ST34 is performed where the processing circuitry 35 determines, on the body mark BM, a position of the region of interest r_mlo in the MLO direction, based on the slice number "#23" indicative of the first tomogram g_mlo(#23) and the total number "40" of the slices of the first tomograms VD_mlo as shown in FIG. 19. This position in the MLO direction is the y-coordinate of the region of interest r_mlo on the body mark BM, and is determined by calculating a value d=23/40 for the ratio of the slice number "#23" with respect to the total slice number "40", and calculating the remaining value c=1−d for the ratio. In other words, the ratio d:c obtained based on the slice number of the first tomogram g_mlo(#23) can be applied to the body mark BM for the vertical axis direction so that the y-coordinate of the region of interest r_mlo on the body mark BM is likewise determined. Step ST34 is thus complete. Note that steps ST33 and ST34 may be performed in reverse order.

Figure 21:
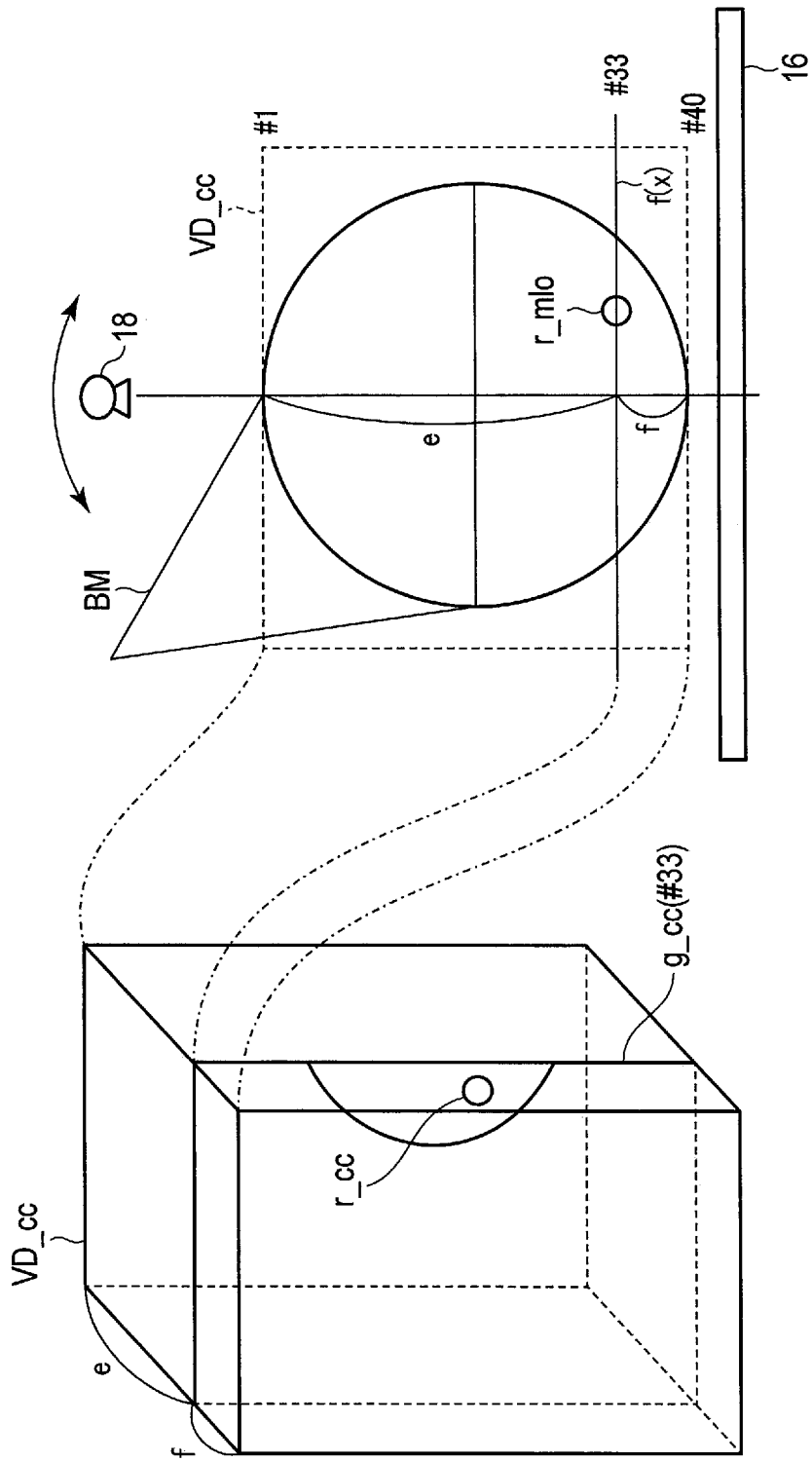
FIG. 21 is a diagram for explaining another exemplary operation according to the first modification of the embodiment.

Subsequent to step ST34, the processing circuitry 35 will locate, on the body mark BM, the intersection between the imaging axis (Y-axis) in the CC direction and a straight line orthogonal to this imaging axis and extending through the determined position (coordinates) of the region of interest r_mlo (step ST35), so as to specify the corresponding second tomogram g_cc(#i) (steps ST36 to ST37). To be more specific, the CC direction-based second tomogram g_cc (#23), which has the same slice number "#23" as the first tomogram g_mlo(#23) including the region of interest r_mlo as shown in FIG. 18, does not include an area corresponding to the region of interest r_mlo as can be seen from FIG. 20. Meanwhile, as shown in FIG. 21, the tomogram that includes an area r_cc corresponding to the region of interest r_mlo, for example, the second tomogram g_cc(#33), conforms to a straight line f(x) that extends through the position of the region of interest r_mlo while being orthogonal to the imaging axis in the CC direction on the body mark BM. Accordingly, step ST35 is employed in order to find out the straight line f(x).

Figure 22:
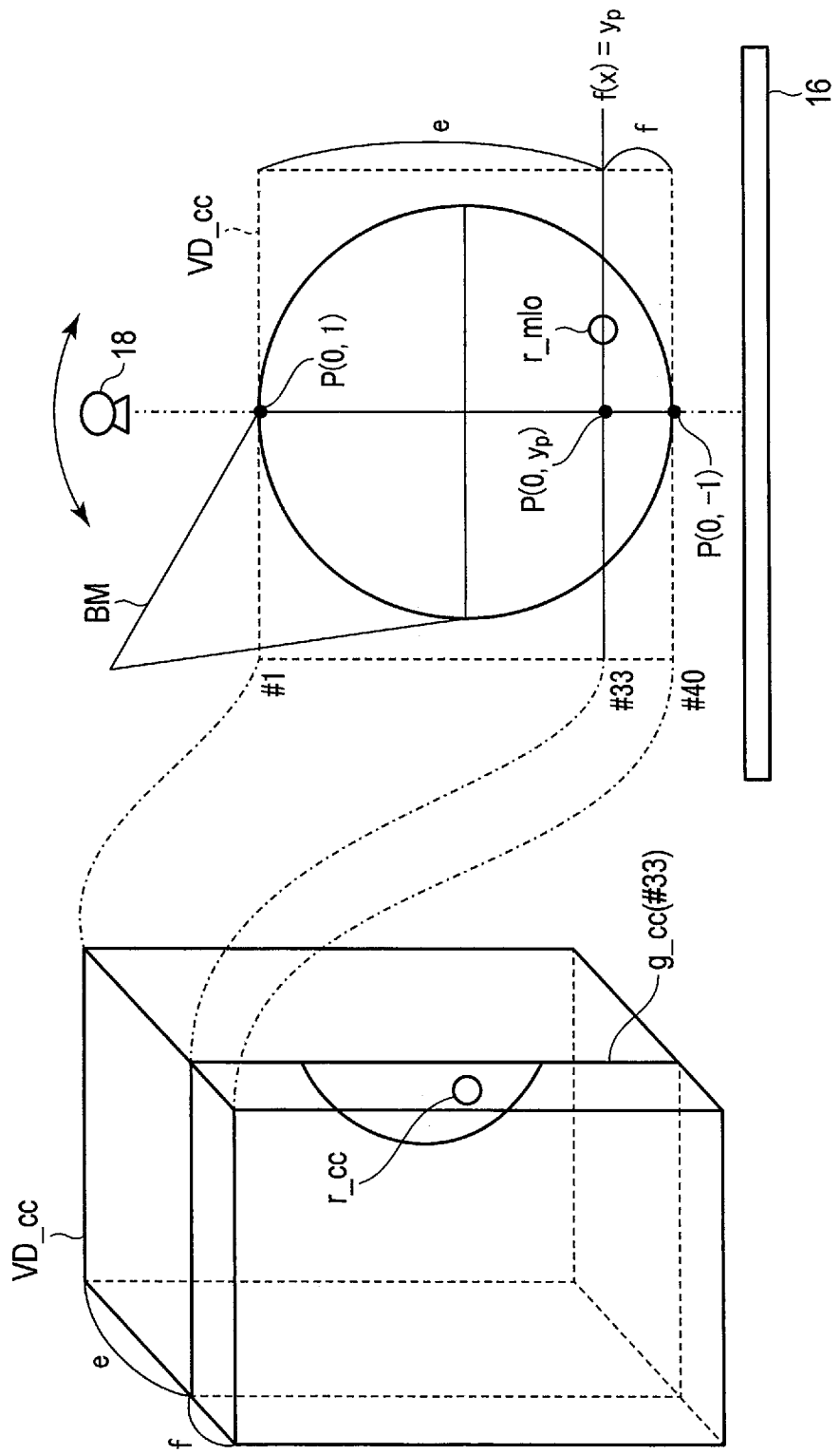
FIG. 22 is a diagram for explaining another exemplary operation according to the first modification of the embodiment.

In step ST35, the processing circuitry 35 locates, on the body mark BM, the intersection P (0, $y_p$) between the imaging axis (Y-axis) in the CC direction and the straight line f(x) extending through the determined position of the region of interest r_mlo and orthogonal to the imaging axis as shown in FIG. 22. Here, the imaging axis is a vertical straight line extending through the origin. Also, the straight line f(x) can be given as f(x)=$y_p$. As such, the y-coordinate $y_p$ of the intersection P is obtained as being equal to the y-coordinate of the region of interest r_mlo. Step ST35 is thus complete.

After step ST35, step ST36 is performed where the processing circuitry 35 calculates a ratio e:f at which the intersection P (0, $y_p$), obtained in step ST35, internally divides the imaging axis within the breast on the body mark BM. The length of the portion e can be given as 1+$y_p$. The length of the portion f can be given as $1-y_p$. Accordingly, the ratio e:f for the internal division is obtained. Step ST36 is thus complete.

After step ST36, step ST37 is performed where the processing circuitry 35 specifies the corresponding second tomogram based on the ratio at which the intersection obtained in step ST35 internally divides the imaging axis within the breast on the body mark BM, and based on the total number of the slices. To be more specific, the processing circuitry 35 specifies the corresponding second tomogram g_cc(#i) by calculating its slice number #i based on the internal division ratio e:f and the total slice number "40", in the manner as previously discussed. The slice number #i here can be calculated as i=e/(e+f)×(total slice number). Accordingly, the processing circuitry 35 specifies the CC direction-based second tomogram g_cc(#33) having a slice number equal to the calculated #33, as the corresponding second tomogram. Step ST37 is complete now. Therefore, step ST30, including steps ST31 to ST37 as described above with reference to FIGS. 18 to 22, is complete. Note that what has been illustrated by FIGS. 18 to 22 is an exemplary case, and step ST30 is not limited to this. In any case, step ST30 is complete upon performing steps ST31 to ST37.

In step ST40 after step ST30, the processing circuitry 35 causes the display 33 to display the first tomogram g_mlo (#23) with the designated region of interest r_mlo and the specified corresponding second tomogram g_cc(#33). The corresponding second tomogram g_cc(#33) includes the area r_cc corresponding to the region of interest r_mlo. Therefore, the operator, etc. can perform diagnostic interpretation with the CC direction-based second tomogram g_cc(#33) that corresponds to the region of interest r_mlo in the MLO direction-based first tomogram r_mlo(#23) for the subject's right breast. When the subject's left breast has already undergone the tomosynthesis imaging, performing steps ST20 to ST40 in the above manner can likewise allow for the interpretation for the breast.

According to the first modification as above, the same effects and advantages as those of the foregoing embodiment can be obtained even when the MLO direction is adopted as the first imaging direction and the CC direction is adopted as the second imaging direction in a manner opposite to the foregoing embodiment.

[Second Modification]

The second modification relates to the instances where the first tomograms are displayed as still images and the second tomograms are displayed as moving images, unlike in the foregoing embodiment that has assumed displaying both the first tomograms and the second tomograms as still images.

Figure 23:
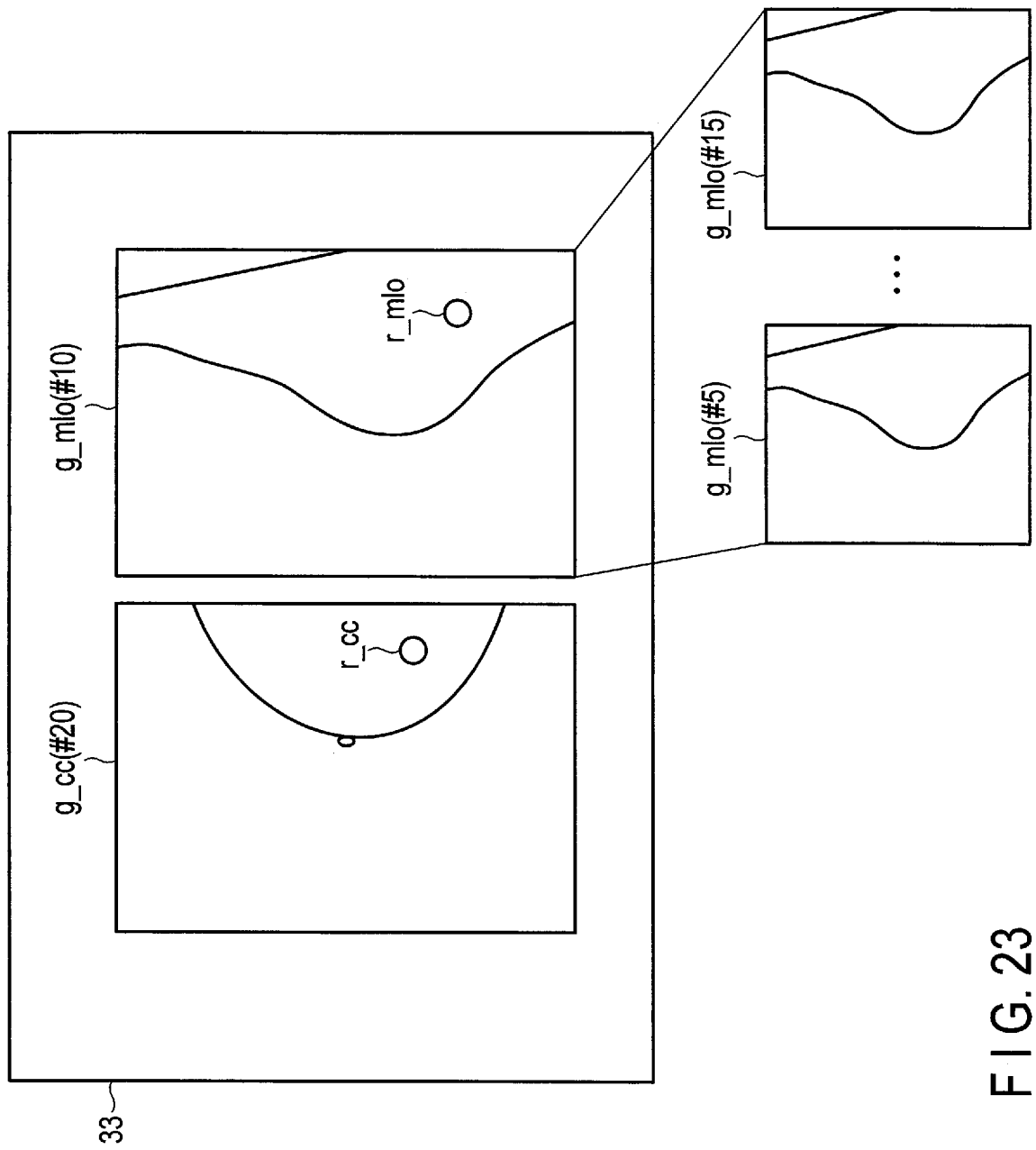
FIG. 23 is a diagram for explaining an exemplary operation according to a second modification of the embodiment.

Accordingly, the processing circuitry 35 of the medical image processing apparatus 30, using the display control function 35*c*, causes the display 33 to display a moving image that includes, for example, a corresponding second tomogram g_mlo(#10) and a predetermined number of second tomograms before and after it as shown in FIG. 23, namely, second tomograms g_mlo(#5), g_mlo(#10), . . . , and g_mlo(#15) in this example. The description here uses the example of applying the display control function 35*c* according to the second modification to the foregoing embodiment as shown in FIG. 23, but this is not a limitation. The display control function 35*c* according to the second modification may also be applicable to the first modification. In this example, also, a moving image including preceding five slices and succeeding five slices is displayed, but this is not a limitation. The number of preceding slices and succeeding slices may be discretionarily determined for the moving image display. In the preceding and succeeding slices for the moving image display, it is preferable that the number of the preceding slices and the number of the succeeding slices are the same, but different numbers may be adopted. Moreover, the display control function 35*c* may switch the display manner of the corresponding second tomogram between still image display and moving image display, according to an operation by the operator, etc.

Similarly, the processing circuitry 26 of the X-ray diagnostic apparatus 1, using the display control function 26*c*, causes the display 27 to display a moving image that includes the corresponding second tomogram and a predetermined number of second tomograms before and after it. The display control function 26*c* may have the same function as the display control function 35*c* discussed above, and may be modified in the similar manner as well.

The remaining aspects are the same as those described for the foregoing embodiment, etc.

According to the second modification as above, the display 33 is caused to display a moving image that includes the corresponding second tomogram and a predetermined number of second tomograms before and after the corresponding second tomogram. Therefore, the second modification realizes not only the same effects and advantages as those of the foregoing embodiment or the first modification, but also an advantage of allowing for diagnostic interpretation with a predetermined number of second tomograms before and after the corresponding second tomogram. Improvement in accuracy of diagnostic interpretation can thus be expected.

[Third Modification]

The third modification relates to the instances where both the first tomograms and the second tomograms are displayed as moving images, unlike in the second modification where the first tomograms are displayed as still images and the second tomograms are displayed as moving images.

Figure 24:
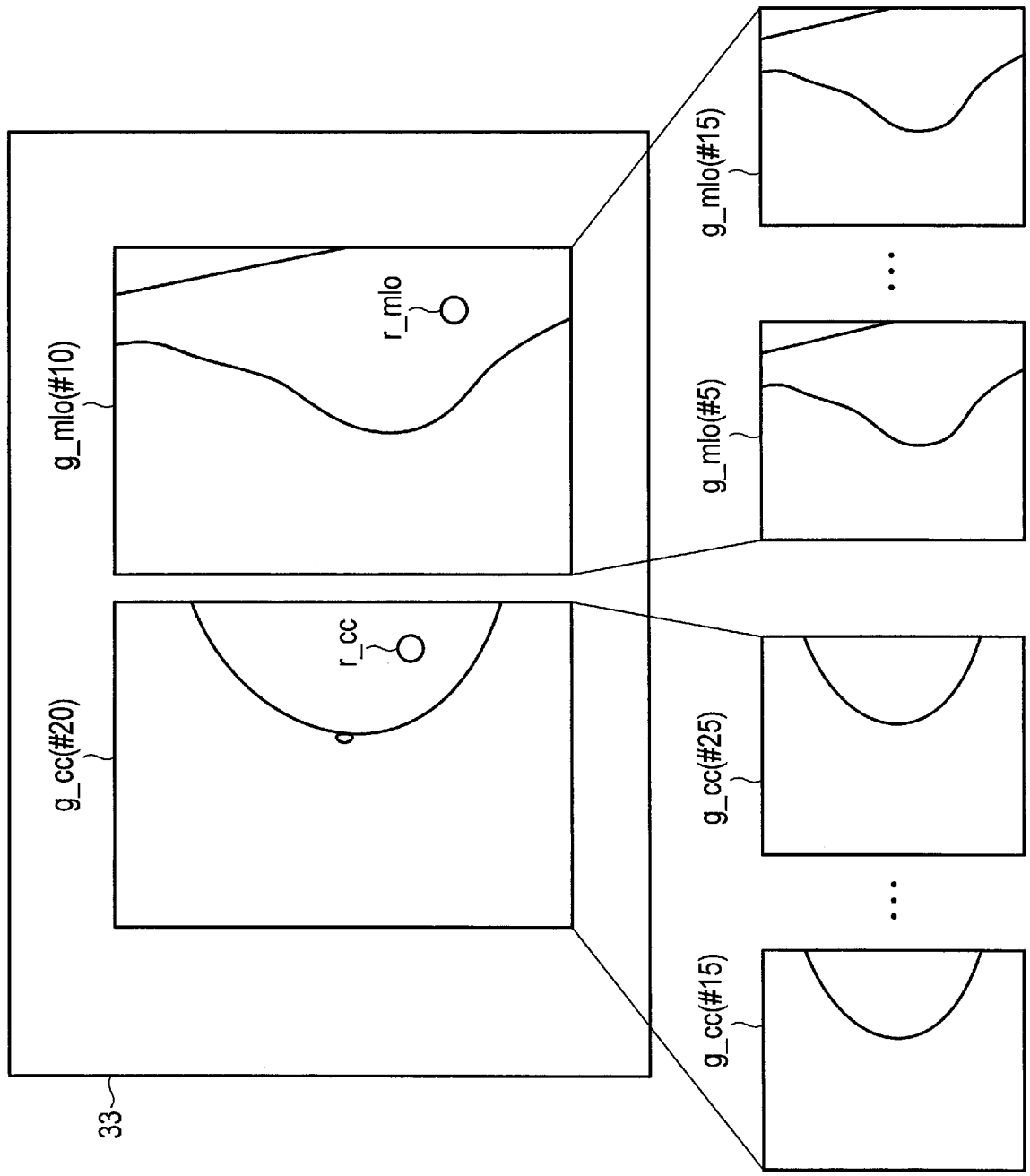
FIG. 24 is a diagram for explaining an exemplary operation according to a third modification of the embodiment.

Accordingly, the processing circuitry 35 of the medical image processing apparatus 30, using the display control function 35*c*, causes the display 33 to display a moving image that includes, for example, one first tomogram g_cc (#20) and a predetermined number of first tomograms before and after it, namely, first tomograms g_cc(#15), . . . , g_cc(#20), . . . , and g_cc(#25), next to the display area for a predetermined number of second tomograms, e.g., second tomograms g_mlo(#5), . . . , g_mlo(#10), . . . , and g_mlo (#15), as shown in FIG. 24. The description here uses the example of applying the display control function 35*c* according to the third modification to the foregoing embodiment as shown in FIG. 24, but this is not a limitation. The display control function 35*c* according to the third modification may also be applicable to the first modification. In this example, also, a moving image including preceding five slices and succeeding five slices is displayed, but this is not a limitation. The number of preceding slices and succeeding slices may be discretionarily determined for the moving image display. In the preceding and succeeding slices for the moving image display, it is preferable that the number of the preceding slices and the number of the succeeding slices are the same, but different numbers may be adopted. Also, for the moving image display, it is preferable that the number of the first tomograms and the number of the second tomograms are the same, but different numbers may be adopted. For the moving image display, further, it is preferable that displaying a first tomogram that includes a designated region of interest and displaying its corresponding second tomogram are synchronized with each other, but asynchronous display is also possible. Moreover, the display control function 35*c* may independently switch the display manner of the first tomograms and the second tomograms between still image display and moving image display, according to an operation by the operator, etc.

Similarly, the processing circuitry 26 of the X-ray diagnostic apparatus 1, using the display control function 26c, causes the display 27 to display a moving image based on the first tomograms, next to a moving image that includes the corresponding second tomogram and a predetermined number of second tomograms before and after it. The display control function 26c may have the same function as the display control function 35c discussed above, and may be modified in the similar manner as well.

The remaining aspects are the same as those described for the foregoing embodiment, etc.

According to the third modification as above, the display is caused to display a moving image that includes one first tomogram and a predetermined number of first tomograms before and after it, next to the display area for a predetermined number of second tomograms. Therefore, the third modification realizes not only the same effects and advantages as those of the second modification of the foregoing embodiment, but also an advantage of allowing for diagnostic interpretation with further use of the associated first tomogram and a predetermined number of first tomograms before and after it. Thus, even more improvement in accuracy of diagnostic interpretation can be expected.

According to at least one embodiment having been described, a region of interest is designated in a first tomogram among multiple tomograms which are based on tomosynthesis imaging performed in the state where the subject is compressed in a first direction. A second tomogram corresponding to this region of interest is specified from among multiple tomograms which are based on tomosynthesis imaging performed in the state where the subject is compressed in a second direction different from the first direction. For example, a region of interest is designated in one of multiple first tomograms acquired by imaging the subject's breast in a first imaging direction. A corresponding second tomogram that includes an area corresponding to this region or interest is specified from among multiple second tomograms acquired by imaging the breast in a second imaging direction different from the first imaging direction. In this manner, the at least one embodiment achieves, beyond the conventional art, an advantageous configuration where only designating a region of interest in the first tomograms acquired in one imaging direction allows for specifying which of the second tomograms acquired in another imaging direction corresponds to the region of interest.

The term "processor" used herein refers to, for example, a central processing unit (CPU) or a graphics processing unit (GPU), or various types of circuitry which may be an application-specific integrated circuit (ASIC), programmable logic device (such as a simple programmable logic device (SPLD), a complex programmable logic device (CPLD), or a field programmable gate array (FPGA)), and so on. The processor reads programs stored in the memory and executes them to realize the respective functions. The programs may be incorporated directly in circuits of the processor, instead of being stored in the memory. According to such implementation, the processor reads the programs incorporated in its circuits and executes them to realize the functions. The embodiments, etc. do not limit the processor to a single circuitry-type processor. A plurality of independent circuits may be combined and integrated as one processor to realize the intended functions. Furthermore, multiple components or features as given in FIGS. 2 and 5 may be integrated as one processor to realize their functions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus, comprising:
    processing circuitry configured to
        designate a region of interest in a first tomogram among multiple tomograms which are based on tomosynthesis imaging performed with a subject compressed in a first direction, and
        specify a second tomogram corresponding to the region of interest from among multiple tomograms which are based on tomosynthesis imaging performed with the subject compressed in a second direction different from the first direction,
    wherein the processing circuitry is further configured to determine, on a schematic diagram schematically expressing the subject, a position of the region of interest in a direction orthogonal to the first direction, based on one end and another end of the subject in the first tomogram,
    wherein the position of the region of interest is determined by calculating, for the schematic diagram, a ratio at which the region of interest internally divides a segment from said one end to said another end of the subject in the first tomogram.

2. The medical image processing apparatus according to claim 1, wherein the processing circuitry is further configured to specify the second tomogram based on the position of the region of interest, and the second direction.

3. The medical image processing apparatus according to claim 1, wherein the processing circuitry is further configured to cause a display to display the specified second tomogram.

4. A medical image processing apparatus, comprising:
    processing circuitry configured to
        designate a region of interest in a first tomogram among multiple tomograms which are based on tomosynthesis imaging performed with a subject compressed in a first direction, and
        specify a second tomogram corresponding to the region of interest from among multiple tomograms which are based on tomosynthesis imaging performed with the subject compressed in a second direction different from the first direction,
    wherein the processing circuitry is further configured to determine, on a schematic diagram schematically expressing the subject, a position of the region of interest in the first direction, based on a slice number indicative of the first tomogram and a total number of slices of said multiple, first direction-based tomograms, and
    wherein the position of the region of interest is determined by calculating a ratio of (1) a ratio of the slice number to the total number, and (2) a remaining value.

5. The medical image processing apparatus according to claim 4, wherein the processing circuitry is further configured to specify the second tomogram by locating, on the schematic diagram, an intersection between an imaging axis in the second direction and a straight line orthogonal to the imaging axis and extending through the determined position of the region of interest.

6. The medical image processing apparatus according to claim 5, wherein the processing circuitry is further configured to calculate a slice number of the second tomogram based on a ratio at which the located intersection internally divides the imaging axis within the subject on the schematic diagram and based on a total number of slices of said multiple, second direction-based tomograms, so that the second tomogram is specified.

7. A medical image processing apparatus, comprising:
processing circuitry configured to
designate a region of interest in a first tomogram among multiple tomograms which are based on tomosynthesis imaging performed with a subject compressed in a first direction, and
specify a second tomogram corresponding to a position of the region of interest from among multiple tomograms which are based on tomosynthesis imaging performed with the subject compressed in a second direction different from the first direction,
wherein the processing circuitry is further configured to cause a display to display the specified second tomogram,
wherein the processing circuitry is further configured to cause the display to display a moving image that comprises the second tomogram and a predetermined number of said multiple, second direction-based tomograms before and after the second tomogram, and
wherein the processing circuitry is further configured to cause the display to switch between a still image display and a moving image display of the second tomogram according to an operation by an operator.

8. The medical image processing apparatus according to claim 7, wherein the processing circuitry is further configured to cause the display to display a moving image that comprises the first tomogram and a predetermined number of said multiple, first direction-based tomograms before and after the first tomogram, next to a display area for a predetermined number of said multiple, second direction-based tomograms.

9. The medical image processing apparatus according to claim 8, wherein the processing circuitry is further configured to cause the display to display the moving image that comprises the second tomogram and a predetermined number of said multiple, second direction-based tomograms before and after the second tomogram, in synchronization with the moving image that comprises the first tomogram and a predetermined number of said multiple, first direction-based tomograms before and after the first tomogram.

10. An X-ray diagnostic apparatus comprising:
processing circuitry configured to
designate a region of interest in a first tomogram among multiple tomograms which are based on tomosynthesis imaging performed with a subject compressed in a first direction, and
specify a second tomogram corresponding to the region of interest from among multiple tomograms which are based on tomosynthesis imaging performed with the subject compressed in a second direction different from the first direction,
wherein the processing circuitry is further configured to determine, on a schematic diagram schematically expressing the subject, a position of the region of interest in a direction orthogonal to the first direction, based on one end and another end of the subject in the first tomogram, and
wherein the position of the region of interest is determined by calculating, for the schematic diagram, a ratio at which the region of interest internally divides a segment from said one end to said another end of the subject in the first tomogram.

11. A non-transitory computer-readable storage medium having stored thereon instructions that, when executed, cause processing circuitry to
designate a region of interest in a first tomogram among multiple tomograms which are based on tomosynthesis imaging performed with a subject compressed in a first direction, and
specify a second tomogram corresponding to the region of interest from among multiple tomograms which are based on tomosynthesis imaging performed with the subject compressed in a second direction different from the first direction,
wherein the instructions, when executed, further cause the processing circuitry to determine, on a schematic diagram schematically expressing the subject, a position of the region of interest in a direction orthogonal to the first direction, based on one end and another end of the subject in the first tomogram, and
wherein the position of the region of interest is determined by calculating, for the schematic diagram, a ratio at which the region of interest internally divides a segment from said one end to said another end of the subject in the first tomogram.

* * * * *